(12) United States Patent
Montes de Oca et al.

(10) Patent No.: US 12,427,283 B2
(45) Date of Patent: Sep. 30, 2025

(54) READY-TO-USE URINARY CATHETER ASSEMBLY

(71) Applicant: Hollister Incorporated, Libertyville, IL (US)

(72) Inventors: Horacio Montes de Oca, Ballina (IE); James J. Fitzpatrick, Ballina (IE); Thomas Renehan, Ballina (IE); Daniel E. O'Brien, Calry (IE); Adam J. Foley, Swords (IE); Shamsedin Rostami, South Cambridgeshire (GB); Enda F. Carter, Galway (IE)

(73) Assignee: Hollister Incorporated, Libertyville, IL (US)

( * ) Notice: Subject to any disclaimer, the term of this patent is extended or adjusted under 35 U.S.C. 154(b) by 311 days.

(21) Appl. No.: 17/742,048

(22) Filed: May 11, 2022

(65) Prior Publication Data

US 2022/0288350 A1    Sep. 15, 2022

Related U.S. Application Data

(62) Division of application No. 16/629,618, filed as application No. PCT/US2018/041639 on Jul. 11, 2018, now Pat. No. 11,376,395.

(60) Provisional application No. 62/531,634, filed on Jul. 12, 2017.

(51) Int. Cl.
    *A61M 25/00*    (2006.01)
    *A61M 25/01*    (2006.01)

(52) U.S. Cl.
    CPC ...... *A61M 25/0017* (2013.01); *A61M 25/002* (2013.01); *A61M 25/0111* (2013.01); *A61M 2025/0046* (2013.01); *A61M 2210/1089* (2013.01)

(58) Field of Classification Search
    CPC ............ A61M 25/002; A61M 25/0017; A61M 25/0111; A61M 39/20; A61M 39/162; A61M 2005/3104; A61M 2210/1089; A61M 2202/0496; A61M 2210/1085; A61M 2210/1096; A61M 39/165; A61M 25/00; A61M 2025/0681; A61M 2210/1078; A61B 90/70; A61B 42/40; A61J 1/1475; A61J 1/1425; A61J 1/1431
    See application file for complete search history.

(56) References Cited

U.S. PATENT DOCUMENTS

| | | | |
|---|---|---|---|
| 3,556,294 A | 1/1971 | Walck | |
| 3,683,928 A | 8/1972 | Kuntz | |
| 3,760,987 A * | 9/1973 | Meterhoefer | B65D 47/06 222/153.07 |
| 3,805,770 A | 4/1974 | Okada | |

(Continued)

FOREIGN PATENT DOCUMENTS

| | | |
|---|---|---|
| EP | 1023882 A1 | 8/2000 |
| EP | 1145729 A1 | 10/2001 |

(Continued)

OTHER PUBLICATIONS

International Search Report and Written Opinion of the International Searching Authority dated Dec. 18, 2018 for International Application No. PCT/US2018/041639.

*Primary Examiner* — Adam Marcetich
(74) *Attorney, Agent, or Firm* — Cook Alex Ltd.

(57) ABSTRACT

Catheter assemblies including a catheter and a liquid.

20 Claims, 14 Drawing Sheets

(56) References Cited

U.S. PATENT DOCUMENTS

| | | | |
|---|---|---|---|
| 3,861,395 A | 1/1975 | Taniguchi | |
| 3,871,358 A | 3/1975 | Fukuda et al. | |
| 3,894,540 A | 7/1975 | Bonner, Jr. | |
| 3,898,993 A | 8/1975 | Taniguchi | |
| 4,051,849 A | 10/1977 | Poncy et al. | |
| 4,140,127 A | 2/1979 | Cianci et al. | |
| 4,170,996 A | 10/1979 | Wu | |
| 4,204,527 A | 5/1980 | Wu et al. | |
| 4,230,115 A | 10/1980 | Walz, Jr. et al. | |
| 4,405,312 A * | 9/1983 | Gross | A61M 39/1011 604/905 |
| 4,533,068 A * | 8/1985 | Meierhoefer | B05B 11/047 222/189.09 |
| 4,564,361 A | 1/1986 | Akiyama | |
| 4,652,259 A | 3/1987 | ONeil | |
| 4,692,154 A | 9/1987 | Singery et al. | |
| 4,784,647 A | 11/1988 | Gross | |
| 4,810,241 A * | 3/1989 | Rogers | A61M 1/285 604/905 |
| 4,811,847 A | 3/1989 | Reif et al. | |
| 4,834,711 A | 5/1989 | Greenfield et al. | |
| 4,886,497 A * | 12/1989 | Scholl, Jr. | A61M 5/3205 604/111 |
| 5,147,341 A | 9/1992 | Starke et al. | |
| 5,230,428 A | 7/1993 | McShane | |
| 5,242,398 A | 9/1993 | Knoll et al. | |
| 5,242,428 A | 9/1993 | Palestrant | |
| 5,334,166 A | 8/1994 | Palestrant | |
| 5,374,248 A * | 12/1994 | Lopez | A61M 39/165 604/82 |
| 5,417,349 A * | 5/1995 | Stull | B65D 47/18 222/562 |
| 5,549,576 A | 8/1996 | Patterson et al. | |
| 5,613,956 A | 3/1997 | Patterson et al. | |
| 5,792,114 A | 8/1998 | Fiore | |
| 5,992,701 A * | 11/1999 | Bougamont | A61F 9/0008 222/189.09 |
| 6,004,305 A | 12/1999 | Hursman et al. | |
| 6,053,892 A * | 4/2000 | Meyer | A61M 5/3202 604/218 |
| 6,053,905 A | 4/2000 | Daignault, Jr. et al. | |
| 6,090,075 A | 7/2000 | House | |
| 6,186,374 B1 * | 2/2001 | Gross | B65D 47/2031 222/494 |
| 6,578,709 B1 | 6/2003 | Kavanagh et al. | |
| 6,602,244 B2 | 8/2003 | Kavanagh et al. | |
| 6,824,015 B1 | 11/2004 | Ammann | |
| 6,848,574 B1 | 2/2005 | Israelsson et al. | |
| 6,986,868 B2 | 1/2006 | Madsen | |
| 7,001,370 B2 | 2/2006 | Kubalak et al. | |
| 7,008,979 B2 | 3/2006 | Schottman et al. | |
| 7,094,220 B2 | 8/2006 | Tanghoj et al. | |
| 7,537,141 B1 * | 5/2009 | Robinson | B65D 47/147 222/569 |
| 7,571,804 B2 | 8/2009 | Kjellmann Bruun et al. | |
| 7,601,158 B2 | 10/2009 | House | |
| 7,662,146 B2 | 2/2010 | House | |
| 7,833,475 B2 | 11/2010 | Madsen | |
| 7,918,831 B2 | 4/2011 | House | |
| 7,938,838 B2 | 5/2011 | House | |
| 7,963,908 B2 | 6/2011 | Lindberg | |
| 8,123,739 B2 | 2/2012 | McQueen et al. | |
| 8,177,774 B2 | 5/2012 | House | |
| 8,317,775 B2 | 11/2012 | House | |
| 8,328,792 B2 | 12/2012 | Nishtala et al. | |
| 8,414,562 B2 | 4/2013 | House | |
| 8,523,843 B2 | 9/2013 | Kavanagh et al. | |
| 8,668,683 B2 | 3/2014 | Golden | |
| 8,771,286 B2 | 7/2014 | House | |
| 8,801,698 B2 | 8/2014 | House | |
| 8,888,747 B2 | 11/2014 | House | |
| 8,968,648 B2 | 3/2015 | Kaneko | |
| 9,314,585 B2 | 4/2016 | Nestenborg et al. | |
| 9,492,631 B2 | 11/2016 | Tanghoj et al. | |
| 9,592,375 B2 * | 3/2017 | Tennican | A61M 39/162 |
| 9,687,629 B1 | 6/2017 | Palmer | |
| 9,821,139 B2 | 11/2017 | Carleo | |
| 9,833,592 B1 | 12/2017 | Palmer | |
| 9,884,167 B2 | 2/2018 | Gustavsson | |
| 2002/0169438 A1 | 11/2002 | Sauer | |
| 2005/0015076 A1 | 1/2005 | Giebmeyer et al. | |
| 2006/0149128 A1 | 7/2006 | Baror | |
| 2007/0088330 A1 | 4/2007 | House | |
| 2008/0051630 A1 | 2/2008 | Levey et al. | |
| 2008/0147049 A1 | 6/2008 | House et al. | |
| 2008/0172042 A1 | 7/2008 | House | |
| 2008/0260576 A1 | 10/2008 | Bruun et al. | |
| 2009/0024111 A1 | 1/2009 | Borodulin et al. | |
| 2009/0028750 A1 * | 1/2009 | Ryan | A61L 2/18 422/292 |
| 2009/0099531 A1 | 4/2009 | Griesbach | |
| 2009/0112064 A1 | 4/2009 | Levey et al. | |
| 2009/0204106 A1 | 8/2009 | Golden | |
| 2009/0306244 A1 | 12/2009 | Belt | |
| 2010/0064456 A1 * | 3/2010 | Ferlic | A61L 2/16 15/210.1 |
| 2010/0198195 A1 | 8/2010 | Nishtala et al. | |
| 2010/0226943 A1 | 9/2010 | Brennan et al. | |
| 2011/0058982 A1 | 3/2011 | Kaneko | |
| 2011/0064512 A1 * | 3/2011 | Shaw | A61B 90/70 401/261 |
| 2011/0114520 A1 | 5/2011 | Matthison-Hansen | |
| 2011/0172592 A1 | 7/2011 | Lee | |
| 2011/0184386 A1 | 7/2011 | House | |
| 2011/0230864 A1 | 9/2011 | House | |
| 2012/0271282 A1 | 10/2012 | Schertiger et al. | |
| 2013/0079755 A1 | 3/2013 | House | |
| 2013/0079756 A1 | 3/2013 | House | |
| 2013/0171030 A1 * | 7/2013 | Ferlic | A61M 39/20 422/294 |
| 2013/0310811 A1 | 11/2013 | Green | |
| 2013/0338603 A1 * | 12/2013 | Roedle | A61J 1/1412 604/199 |
| 2014/0224678 A1 * | 8/2014 | Schertiger | A61M 25/002 206/210 |
| 2014/0227144 A1 | 8/2014 | Liu et al. | |
| 2014/0262859 A1 | 9/2014 | Knapp et al. | |
| 2015/0018805 A1 * | 1/2015 | House | A61M 25/0017 604/544 |
| 2015/0273116 A1 | 10/2015 | Knapp et al. | |
| 2015/0306342 A1 | 10/2015 | Rostami et al. | |
| 2015/0306369 A1 * | 10/2015 | Burkholz | A61M 39/162 604/539 |
| 2015/0320970 A1 | 11/2015 | Foley et al. | |
| 2015/0343171 A1 | 12/2015 | Hannon | |
| 2015/0352321 A1 | 12/2015 | Hannon et al. | |
| 2016/0022244 A1 | 1/2016 | Courtney et al. | |
| 2016/0038717 A1 | 2/2016 | Murray et al. | |
| 2016/0144118 A1 * | 5/2016 | Solomon | A61M 5/30 206/370 |
| 2016/0213880 A1 | 7/2016 | Oflynn et al. | |
| 2016/0339205 A1 | 11/2016 | Foley et al. | |
| 2017/0000978 A1 | 1/2017 | Murray et al. | |
| 2017/0007802 A1 | 1/2017 | Clarke et al. | |
| 2017/0143447 A1 * | 5/2017 | Rogers | A61M 39/16 |
| 2017/0165467 A1 * | 6/2017 | Chiu | A61M 39/162 |
| 2018/0071508 A1 * | 3/2018 | Drmanovic | A61M 39/18 |
| 2018/0085568 A1 | 3/2018 | Drmanovic | |
| 2018/0170631 A1 * | 6/2018 | Hawry | B65D 25/42 |
| 2018/0250194 A1 * | 9/2018 | Drmanovic | A61L 2/18 |
| 2019/0009074 A1 * | 1/2019 | Drmanovic | A61J 1/2048 |
| 2019/0321212 A1 | 10/2019 | Palmer | |
| 2021/0299410 A1 | 9/2021 | Wiesman | |

FOREIGN PATENT DOCUMENTS

| | | | |
|---|---|---|---|
| EP | 1757251 A2 | 2/2007 | |
| EP | 2140903 A1 | 1/2010 | |
| EP | 3078393 A1 | 10/2016 | |
| GB | 2296182 A * | 6/1996 | A47L 25/00 |
| NO | 9534341 A1 | 12/1995 | |
| WO | 9806642 A1 | 2/1998 | |

(56) References Cited

FOREIGN PATENT DOCUMENTS

| | | |
|---|---|---|
| WO | 2005092418 A1 | 10/2005 |
| WO | 2010003419 A2 | 1/2010 |
| WO | 2011011023 A1 | 1/2011 |
| WO | 2011076217 A1 | 6/2011 |
| WO | 2015084923 A1 | 6/2015 |
| WO | 2015089189 A2 | 6/2015 |

* cited by examiner

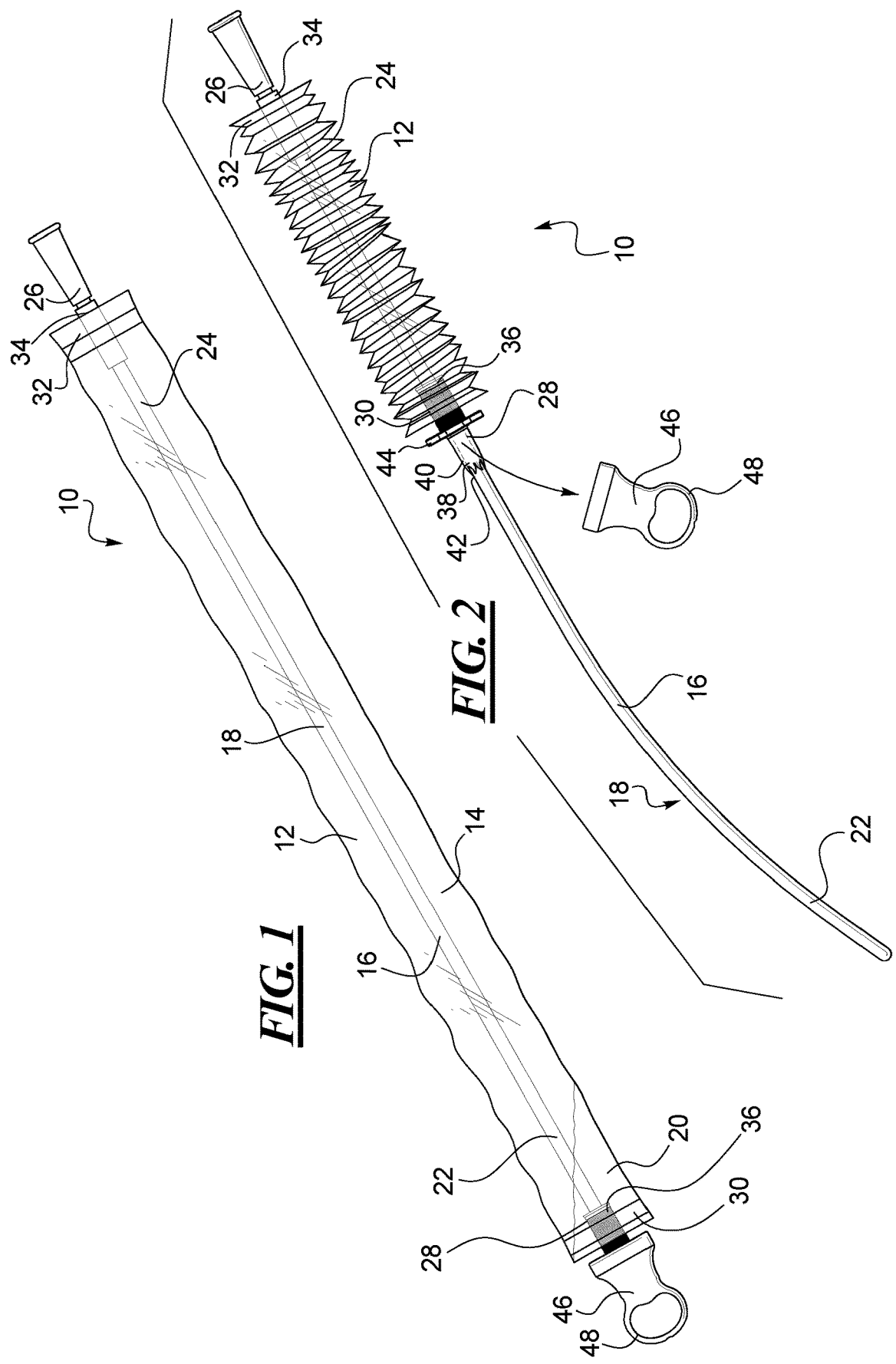

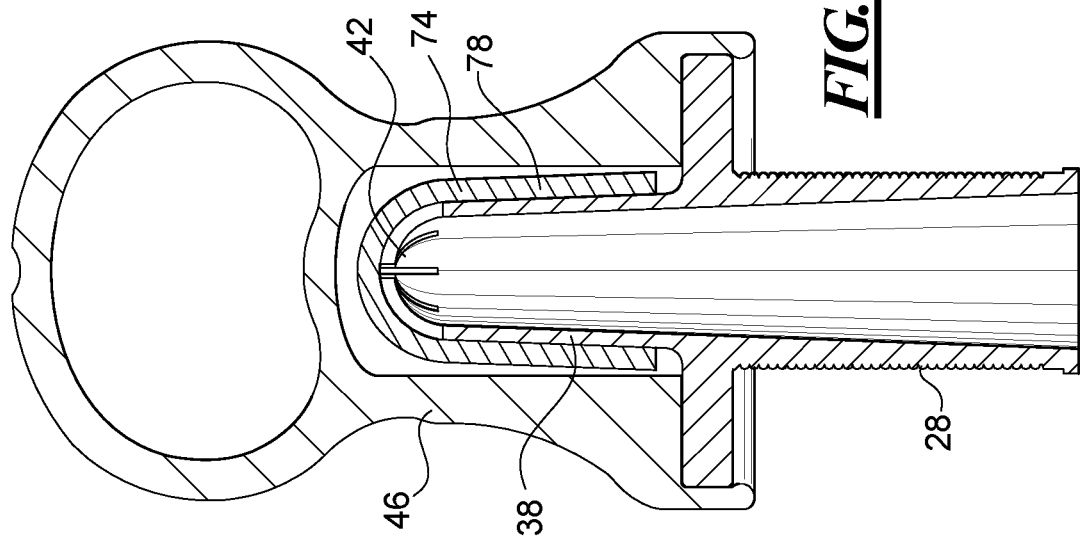
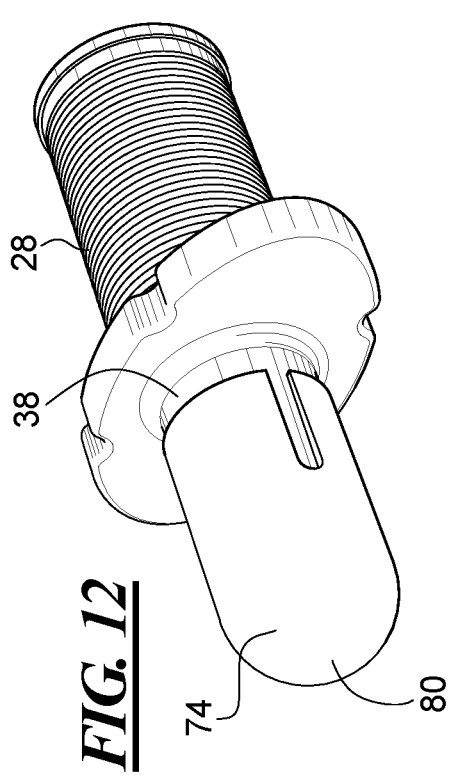
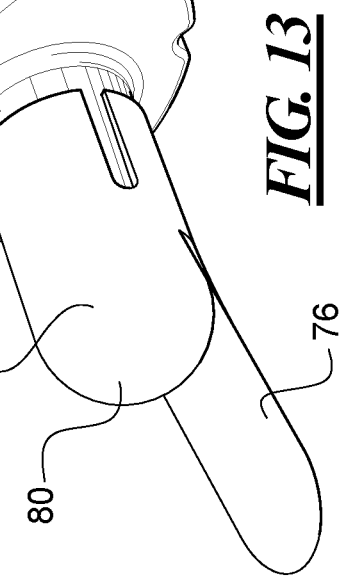

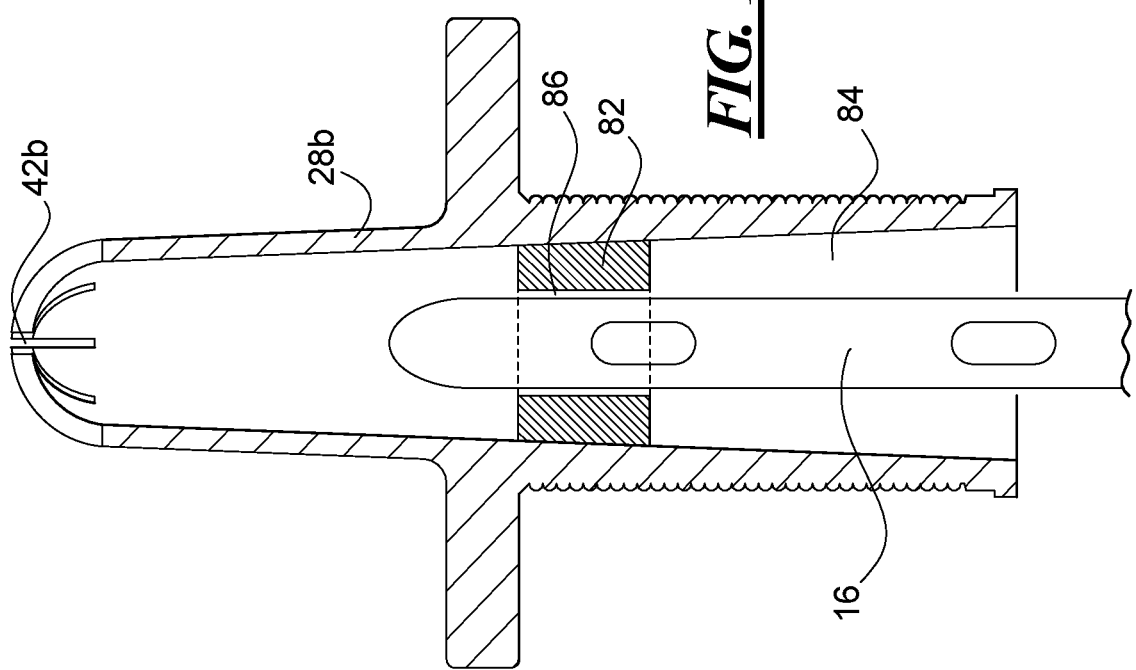
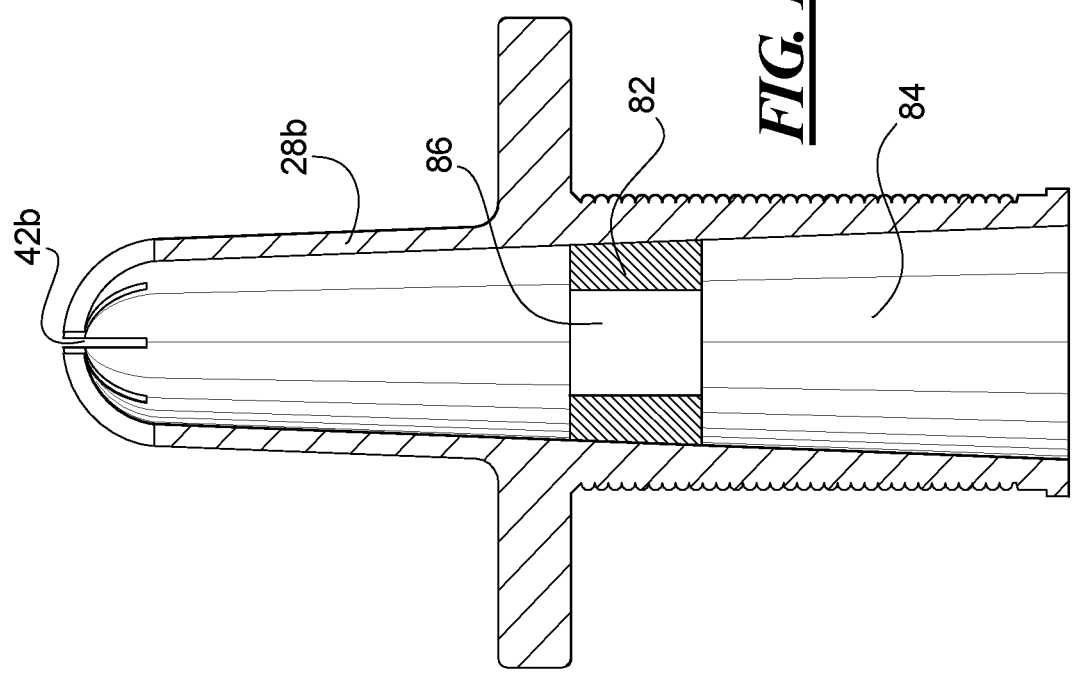

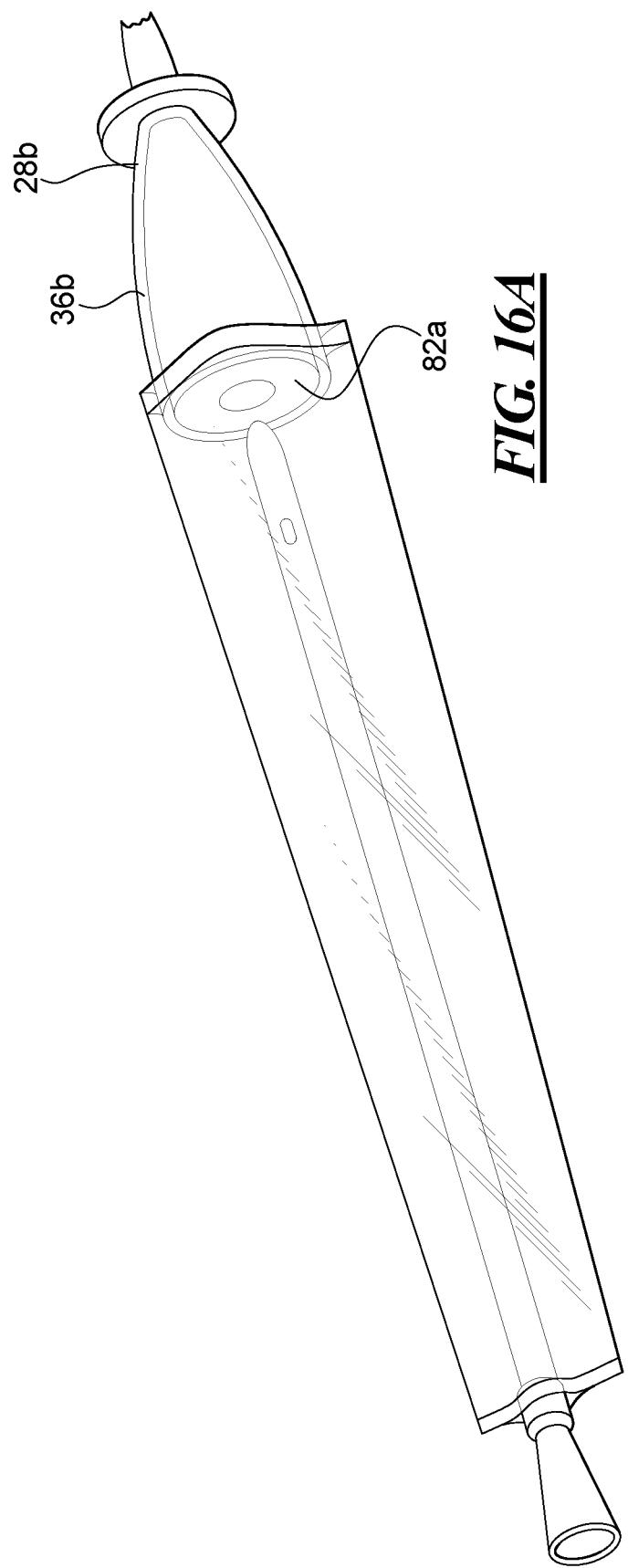

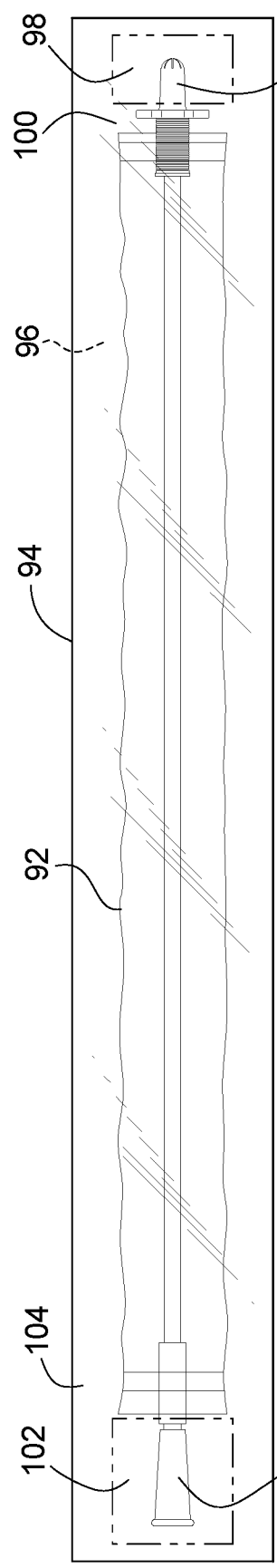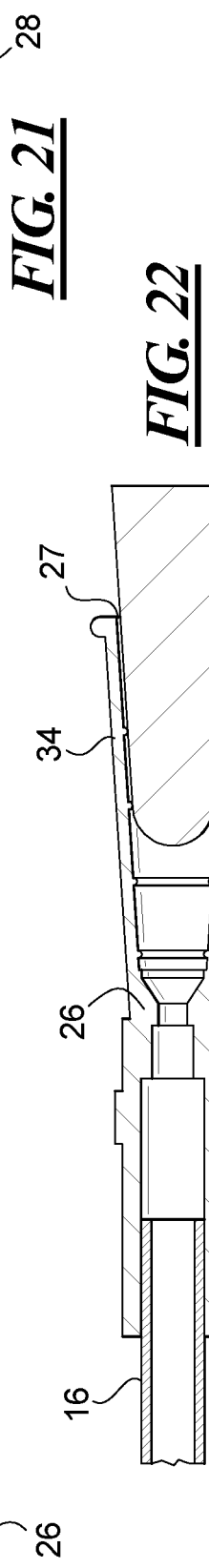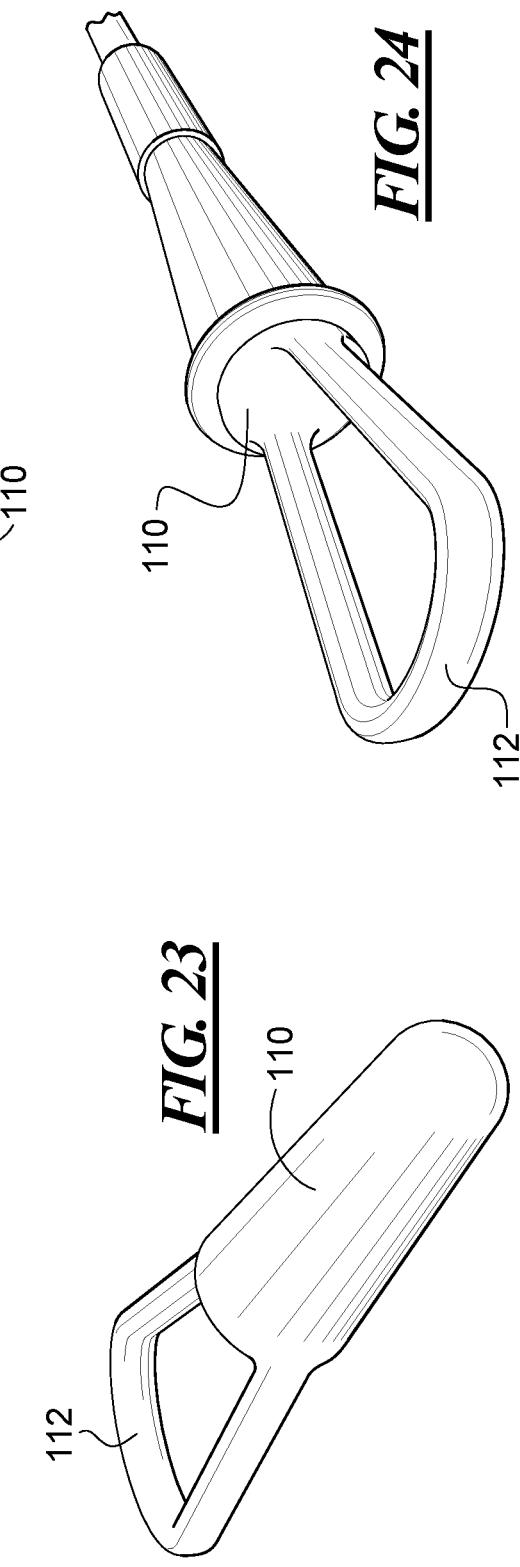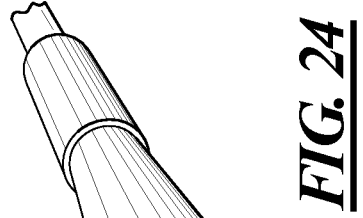

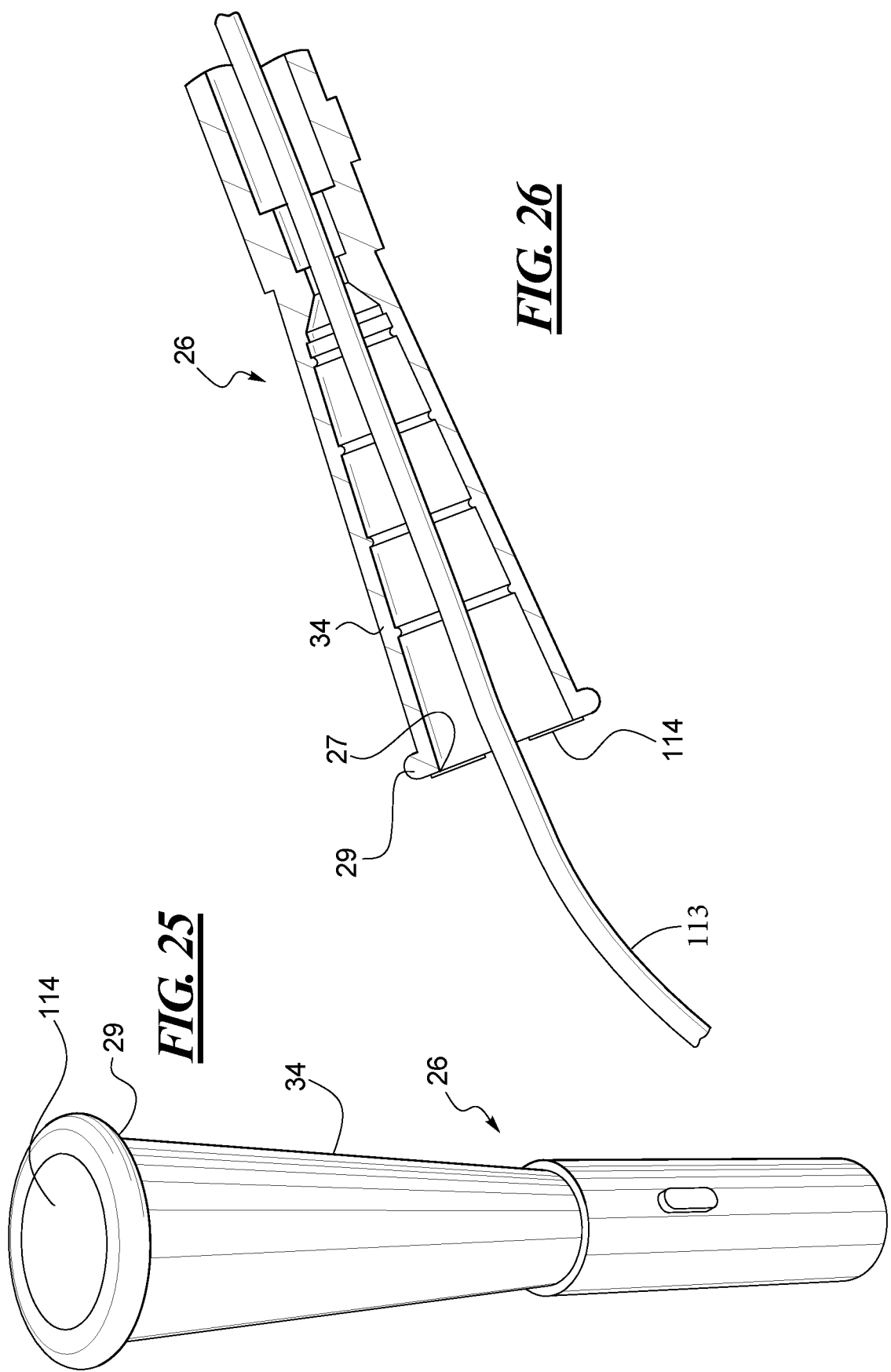

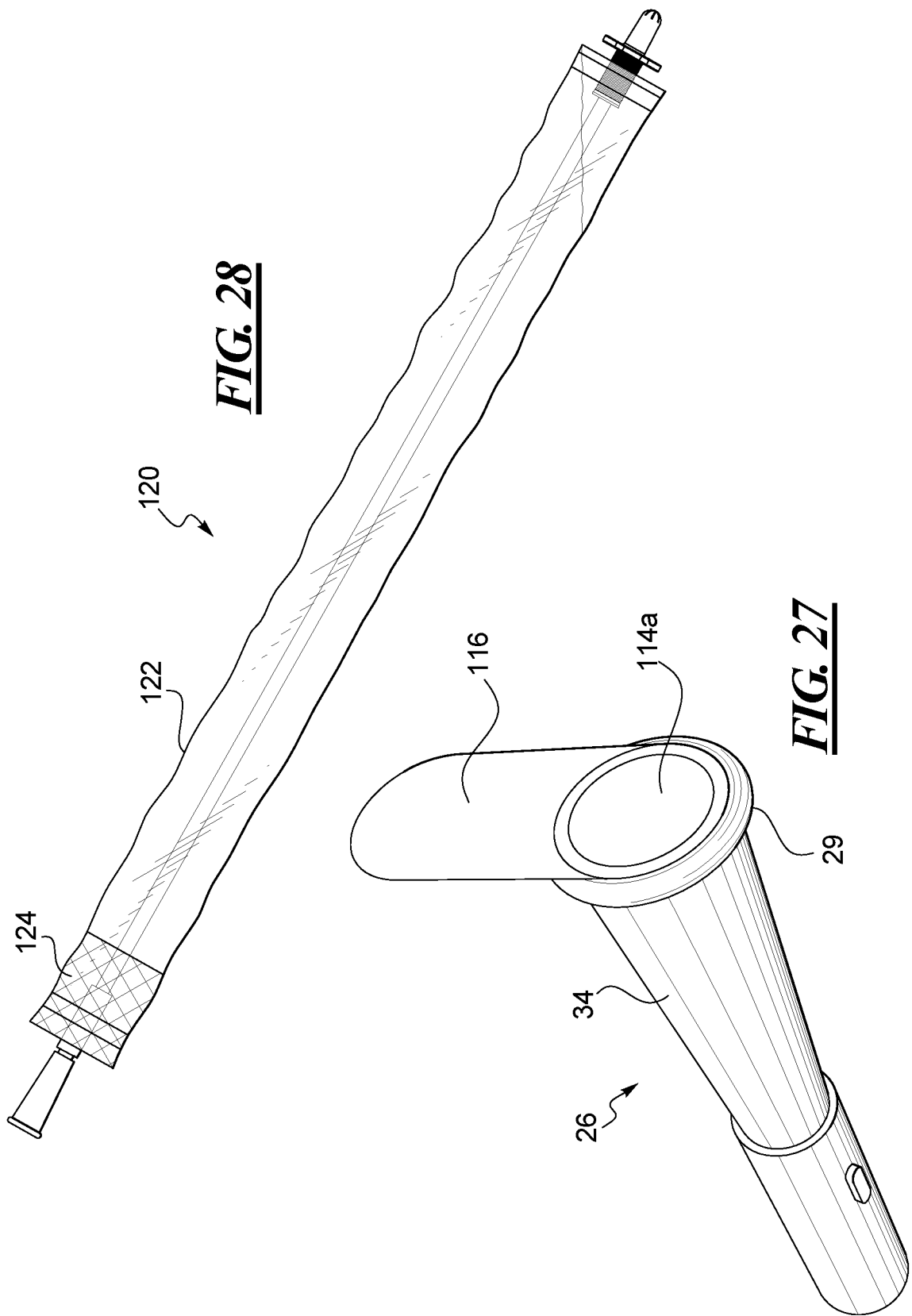

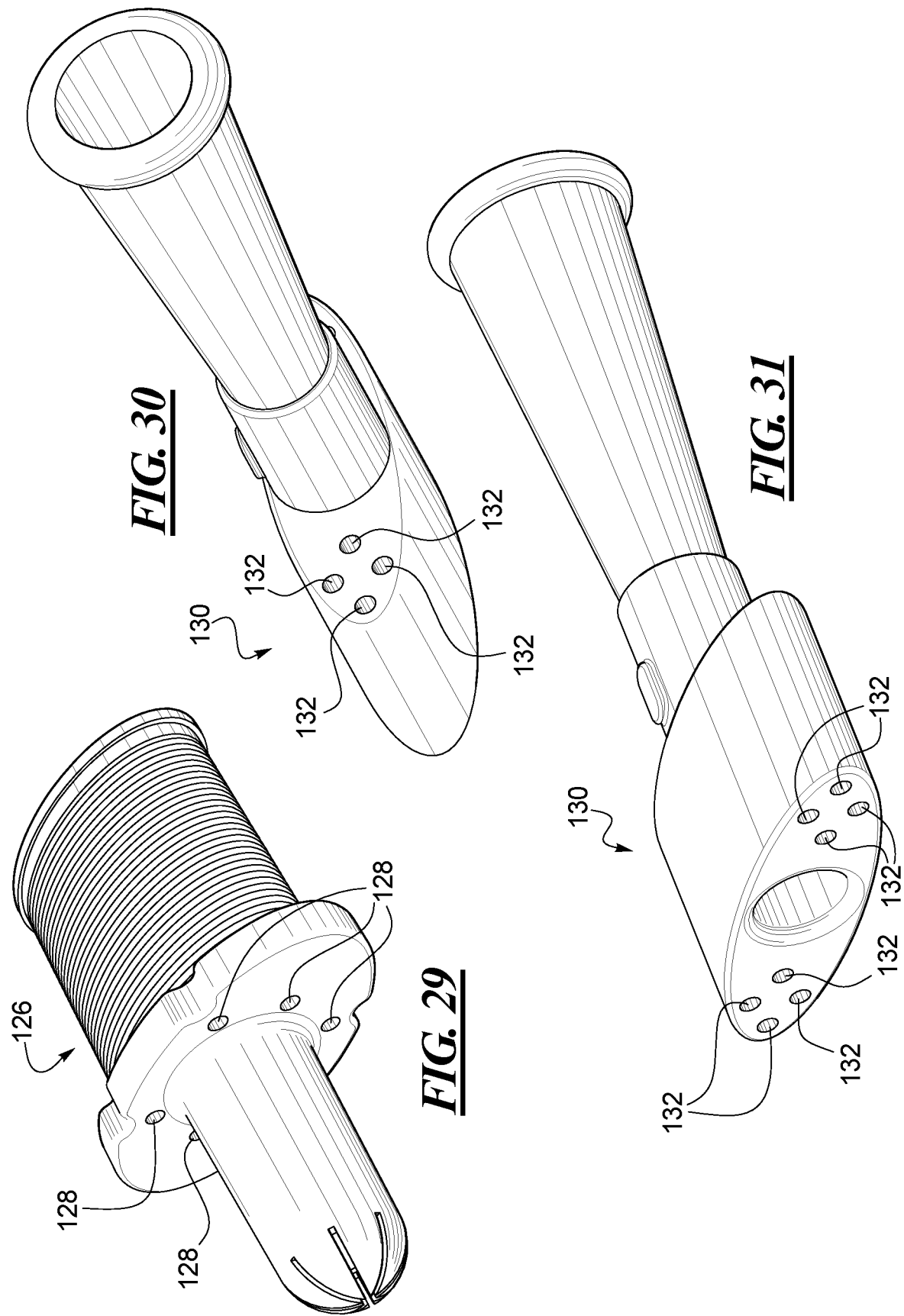

READY-TO-USE URINARY CATHETER ASSEMBLY

RELATED APPLICATIONS

This is a Divisional application of U.S. application Ser. No. 16/629,618, filed Jan. 9, 2020, which is the U.S. National Stage Application of PCT Application No. PCT/US2018/041639, filed Jul. 11, 2018, which claims the benefit of and priority to U.S. Provisional Patent Application No. 62/531,634, filed Jul. 12, 2017, all of which are hereby incorporated herein by reference.

FIELD OF THE DISCLOSURE

The present disclosure generally relates to ready-to-use catheter assemblies, and more particularly, to ready-to-use catheter assemblies that include a sleeve containing a hydrophilic catheter and a lubricity enhancing liquid.

BACKGROUND

It is desirable for medical devices that are inserted into the body to have a lubricated or lubricious outer surface to facilitate insertion into and/or removal of the medical device from the body. Such devices may include, for example, urinary catheters, endoscopes, cardiovascular catheters, syringes, vascular stents, etc. Such medical devices may have a hydrophilic coating or layer disposed on an outer surface thereof. Hydrophilic coatings are becoming the preferred method of providing lubricious surfaces because of their high lubricity and ease of use. Hydrophilic coatings become slippery or lubricous when wetted with a wetting fluid, such as saline or water. The wetted lubricous hydrophilic coating eases insertion and removal of the device, which can result in minimizing soft tissue damage and reducing overall discomfort during use of the medical device.

When a hydrophilically coated medical device is used, the hydrophilic coating is wetted with a wetting fluid prior to use to activate the hydrophilic coating. For example, the user may contact the hydrophilic coating with a liquid wetting fluid to wet or activate the coating. It is also becoming quite common to provide catheter assemblies that include the medical device and liquid wetting fluid within the cavity of a package. In one type of package, the wetting fluid may be loose within the package and in contact with the hydrophilic medical device during storage and distribution of the package. In another type of package, the medical device and an openable sachet or pouch that contains the wetting fluid may be located within the package. In this second type of package the user bursts open the sachet within the package just prior to use. After the sachet is burst open, the wetting fluid is released and is loose within the package wherein it contacts and wets the hydrophilic medical device.

In packages that contain a lubricity enhancing liquid, such as a wetting fluid, the liquid is either initially loose within the package or becomes loose after being released from a sachet. Because these packages include loose liquid at the time of opening the package, there is a risk of liquid spillage upon opening the package and removal of the medical device from the package. Such spillage may cause a mess, which can require clean up. In some instances, the liquid may include additives that can undesirably stain the clothes of the user.

Therefore, there remains a need for improved medical device assemblies for containing medical devices and a liquid, wherein the medical device assembly assists in reducing the risk of liquid spillage.

SUMMARY

In one aspect, a catheter assembly that includes a urinary catheter having a proximal end portion and a distal end portion. The urinary catheter has a catheter shaft including a proximal insertion end portion and a distal end portion having a drainage member associated with the distal end portion of the catheter shaft. The urinary catheter also has a hydrophilic surface. The assembly further includes a collapsible sleeve defining a compartment that contains at least a portion of the catheter shaft. The distal end portion of the sleeve is attached to the distal end portion of the urinary catheter. For example, the sleeve may be attached to the drainage member and/or the distal end portion of the catheter shaft. An amount of liquid is located within the compartment of the sleeve and in contact with the hydrophilic surface. An introducer is located at the proximal end portion of the sleeve wherein the introducer includes a passageway therethrough and a proximal opening for passage of the catheter shaft therethrough. A removable cap covers the introducer wherein the cap includes an anti-leak element. In one embodiment, the introducer may also include an anti-leak element. The anti-leak elements disclosed herein may prevent leakage of the liquid, substantially prevent leakage or reduce the risk of leakage.

In another aspect, a catheter assembly that includes a urinary catheter having a proximal end portion and a distal end portion. The urinary catheter also has a catheter shaft including a proximal insertion end portion and a distal end portion having a drainage member associated with the distal end portion of the catheter shaft. The urinary catheter also has a hydrophilic surface. The assembly further includes a collapsible sleeve defining a compartment that contains at least a portion of the catheter shaft. The distal end portion of the sleeve is attached to the distal end portion of the urinary catheter. An amount of liquid is located within the compartment of the sleeve and in contact with the hydrophilic surface. An introducer is located at a proximal end portion of the sleeve wherein the introducer includes a passageway therethrough and a proximal opening for passage of the catheter shaft therethrough. The assembly also includes a removable cap covering the at least the opening of the introducer.

In another aspect, a catheter assembly includes a urinary catheter having a proximal end portion and a distal end portion. The urinary catheter also has a catheter shaft including a proximal insertion end portion and a distal end portion having a drainage member associated with the distal end portion of the catheter shaft. The urinary catheter also has a hydrophilic surface. The assembly further includes a collapsible sleeve defining a compartment that contains at least a portion of the catheter shaft. The distal end portion of the sleeve is attached to the distal end portion of the urinary catheter. An amount of liquid is located within the compartment of the sleeve and in contact with the hydrophilic surface. An introducer is located at a proximal end portion of the sleeve wherein the introducer includes a passageway therethrough and a proximal opening for passage of the catheter shaft therethrough. The assembly also includes an absorbent material located within the passageway of the introducer.

In another aspect, a catheter assembly that includes a urinary catheter having a proximal end portion and a distal end portion. The urinary catheter also has a catheter shaft including a proximal insertion end portion and a distal end portion having a drainage member associated with the distal end portion. The urinary catheter also has a hydrophilic surface. The assembly further includes a collapsible sleeve defining a compartment that contains at least a portion of the catheter shaft. The distal end portion of the sleeve is attached to the distal end portion of the catheter. An amount of liquid is located within the compartment of the sleeve and in contact with the hydrophilic surface. An introducer is located at a proximal end portion of the sleeve wherein the introducer includes a passageway therethrough and a proximal opening for passage of the catheter shaft therethrough. The assembly also includes a vent for venting gases from the compartment defined by the sleeve.

In another aspect, a catheter assembly that includes a urinary catheter having a catheter shaft including a proximal insertion end portion and a distal end portion having a drainage member associated with the distal end portion. The urinary catheter also has a hydrophilic surface. The assembly further includes a collapsible sleeve formed from front and back sheets. The sleeve defines a proximal compartment containing an introducer, an intermediate compartment containing the catheter shaft and a distal compartment containing at least a portion of a drainage member. The assembly also includes an amount of liquid located within the intermediate compartment of the sleeve and in contact with the hydrophilic surface.

BRIEF DESCRIPTION OF DRAWINGS

FIG. 1 is a plan view of one embodiment of a catheter assembly in accordance with the present disclosure;

FIG. 2 is perspective view of the catheter assembly of FIG. 1 shown with the sleeve in a collapsed configuration;

FIG. 12 is a perspective view of a cap in accordance with the present disclosure, wherein the cap is engaged with the introducer;

FIG. 13 is a perspective view of an embodiment of the cap of FIG. 12 wherein the cap includes a pull tab for removal of the cap from the introducer;

FIG. 14 is a cross-sectional view of an introducer including the cap of FIG. 12 or FIG. 13 and a second cap thereover;

FIG. 15 is a cross-sectional view of one embodiment of an introducer in accordance with the present disclosure;

FIG. 16 is a cross-sectional view of the introducer of FIG. 15 shown with a catheter inserted therein;

FIG. 16A is another embodiment of a catheter assembly in accordance with the present disclosure;

FIG. 21 is a plan view of another embodiment of a catheter assembly in accordance with the present disclosure;

FIG. 22 is a cross-sectional view of the drainage end portion of a urinary catheter shown with a plug inserted into the opening of the drainage member of the catheter in accordance with the present disclosure;

FIG. 23 is a perspective view of one embodiment of a plug in accordance with the present disclosure;

FIG. 24 is a perspective view of the plug of FIG. 23 shown inserted into the opening of a drainage member;

FIG. 25 is a perspective view of a drainage member of a catheter including a cover over the drainage opening;

FIG. 26 is a cross-sectional view of the drainage member of FIG. 25 showing urine passing through a dissolved portion of the cover;

FIG. 27 is a perspective view of a drainage member of a catheter wherein the drainage member has a cover over the drainage opening and the cover includes a pull tab for removing the cap;

FIG. 28 is another embodiment of a catheter assembly in accordance with the present disclosure;

FIG. 29 is a perspective view of an introducer in accordance with the present disclosure wherein the introducer includes vents;

FIGS. 30 and 31 are perspective views of a drainage member in accordance with the present disclosure wherein the drainage member includes vents.

DETAILED DESCRIPTION OF THE EMBODIMENTS

Figure 4:
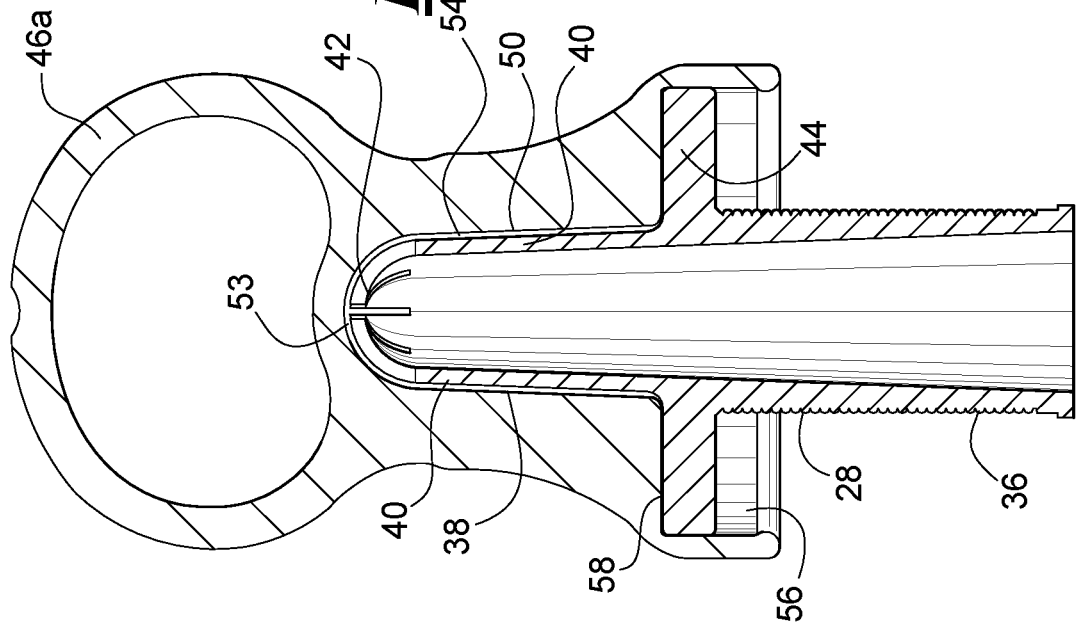
FIG. 4 is a cross-sectional view of the cap of FIG. 3 shown engaged with an introducer of a catheter assembly.

The present disclosure is generally directed to ready-to-use catheter assemblies that include a sleeve forming a compartment containing a catheter and a lubricity enhancing liquid in contact with the catheter. In one embodiment, the catheter may be a hydrophilic catheter wherein the liquid is a wetting fluid that hydrates the hydrophilic catheter or an activation fluid that activates or renders the hydrophilic catheter lubricous. The wetting fluid may be saline or water, and the activation fluid may be short chain diols and/or triols such as ethylene glycol and glycerol and their mixtures with water and a free radical scavenger capable of inhibiting the photochemical reaction between water and the hydrophilic coating. In one embodiment, the activation fluid may be propylene glycol/water mixtures. When included, the free radical scavenger may be vitamin C, vitamin D or other known biocompatible antioxidants known in the art.

The catheter assemblies also include various anti-leak features that reduce or prevent spillage/leakage of the liquid and/or ease the use of the assembly. It will be readily understood by those of ordinary skill that while these features may be described individually, that such features and various embodiments described herein may be combined with each other to form a catheter assembly. For example, features of the caps, introducers, drainage members, plugs, sleeves, packaging, etc. are not mutually exclusive and may be combined with each other in a catheter assembly. For example, the features illustrated in FIGS. 3 and 5 may be combined. In another example, the features shown in FIGS. 3, 5, 7, 9, 12, 13, 15, 19, 21, 22, 23, 25, 28, 29, 30, 32 and 33 are not mutually exclusive and may be mixed or matched to form a catheter assembly.

FIGS. 1 and 2 illustrate an embodiment of a ready-to-use urinary catheter assembly 10. The catheter assembly 10 may be variously configured without departing from the scope of the present disclosure, but in one embodiment, the catheter assembly 10 includes a sleeve 12, which may be made from a flexible polymeric material, such as, but not limited to, low density polyethylene and/or linear low density polyethylene. The sleeve defines a cavity or compartment 14 that contains at least an insertable portion of the shaft 16 of a catheter 18 and a liquid 20 for enhancing the lubricity of the catheter. In one embodiment, the catheter shaft 16 includes a hydrophilic surface on at least the insertable portion of the shaft. For example, the catheter shaft 16 may be made of a hydrophilic material or may have a hydrophilic coating disposed on the outer surface of the shaft 16. The liquid 20 may be a wetting fluid or activation fluid that is in direct contact with the hydrophilic surface of the catheter shaft 16 and wets/activates the hydrophilic surface, thereby rending the surface very lubricious. The catheter shaft 16 also includes a proximal insertion end portion 22 and a distal end portion 24. A drainage member 26, such as a funnel is associated with the distal end portion 24 of the catheter shaft 16.

An introducer 28 is secured or sealed to a proximal end 30 of the sleeve 12, with an opposite or distal end 32 of the sleeve 12 being secured or sealed by a distal end portion of the urinary catheter. As shown in FIG. 1, the sleeve may be attached to the proximal end portion 34 of the drainage member 26. In another embodiment, the sleeve may be attached to the distal end portion 24 of the catheter shaft 16, or attached to both the drainage member and the distal end portion of the catheter shaft. The sleeve 12 is secured to the introducer 28 and the distal end portion of the catheter in a manner that seals or closes off the proximal and distal ends 30 and 32 of the sleeve 12 such that the liquid 20 remains contained within the compartment 14 defined by the sleeve 12 or reduces the possibility of leakage. The ends 30 and 32 of the sleeve 12 may be sealed or partially attached to the introducer 28 and the distal end portion of the catheter by, for example, heat sealing, sonic welding, adhesive, etc.

The introducer 28 extends between a distal end 36 and a proximal end 38 (FIGS. 2 and 4). The introducer 28 is sealingly connected or secured to the sleeve 14 at or adjacent to the distal end 36 of the introducer. The proximal end 38 of the introducer 28 includes an insertion tip 40 that is configured to be inserted into the urethral opening. The proximal end 38 of the introducer 28 may include an aperture or opening 42 (FIG. 4) that may be moved between a closed configuration (in which the catheter is fully positioned within the sleeve and introducer and there is no other object positioned within the opening 42) and an open configuration (in which the catheter or any other object is partially positioned within or extending through the opening 42, with a portion of the object positioned within the introducer and another portion positioned outside of the introducer (FIG. 2)). In one embodiment, the opening 42 is provided as a slit opening with one or more slits or cuts defining a plurality of deformable petals that may be moved to define the aforementioned open and closed configurations. In other embodiments, the opening 42 may be differently configured, provided that it is configured to allow passage of the catheter therethrough. A radially extending flange 44 is located in the mid-section of the introducer 28. The flange 44 may act as a stop that contacts the glans penis to prevent over insertion of the insertion tip 40. That is, the flange 40 may include a front surface that contacts the glans penis to prevent over insertion. The flange 40 may also include a back surface that may be contacted by the user's fingers to aid in insertion of the insertion tip 40.

The catheter assembly 10 may further include a cap 46 configured to be removably connected to the introducer 28 and cover the proximal end 38 thereof. Optionally, the cap 46 may include a ring-shape proximal end 48 that the user may grasp during removal of the cap 46 to expose the insertion tip 40.

Referring to FIG. 2, in use, the cap 46 is removed from the introducer 28 and the insertion tip 40 of the introducer 28 is inserted into the urethral opening. The user may then grip the catheter shaft 16 through the sleeve 12 and advance the shaft 16 through the opening 42 of the introducer 28 to advance the catheter shaft 16 through the urethra to access the bladder. As the catheter shaft 16 is advanced through the opening 42 of the introducer 28, the sleeve 12 collapses or folds upon itself around the distal end portion 24 of the catheter shaft 16.

The catheter assembly 10 may be contained in an outer package which is distributed to an end user, or the sleeve 12 may be the outer package. When the sleeve 12 is the outer package it may be made from a low vapor transmission material, such as, but not limited to, a polymeric/metal laminate film. One such film may be a polymeric/aluminum laminate film.

One issue that may occur with catheter assemblies of the type illustrated in FIG. 1 is that the liquid 20 may leak from the catheter assembly 10 during storage, distribution, or use by the end user. If the catheter assembly 10 leaks liquid 20, this may result in undesired spillage of the liquid during use. The remaining figures illustrate features and various embodiments that assist in reducing the risk of accidental liquid spillage and/or aid in the ease of use of the catheter assembly. As mentioned above, while the features and embodiments shown in these figures and described in more detail below may be individually described, such features and embodiments may be combined or mixed and matched in a catheter assembly.

Figure 3:
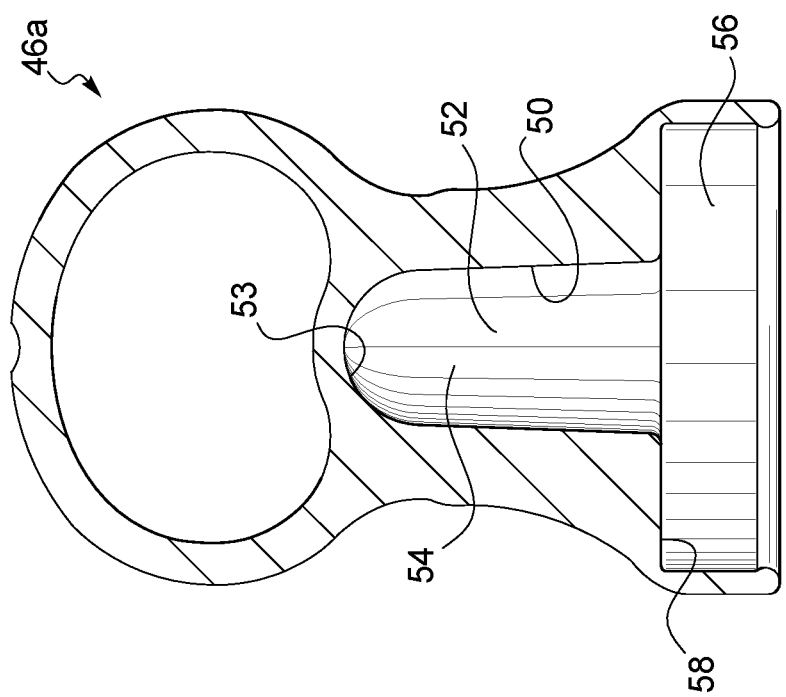
FIG. 3 is a cross-sectional view of one embodiment of a cap in accordance with the present disclosure.

Turning now to FIGS. 3 and 4, these figures illustrate one embodiment of a cap 46a that has similar features to that of cap 46 and that includes features that reduce the risk of liquid leaking from the catheter assembly during storage and distribution of the catheter assembly. The cap 46a includes an inner surface 50 that defines a cavity 52 that is configured to receive the introducer 28. The cavity 52 includes a proximal compartment 54 and a distal compartment 56 separated by a shoulder 58. As illustrate in FIG. 4, the proximal compartment 54 of the cavity 52 defined by the inner surface 50 is sized and shaped to closely conform to or be commensurate with the size and shape of the proximal insertion tip 40 of the introducer 28. In one embodiment, inner surface 50 of the cap 46a may abut at least a portion the proximal insertion tip 40 of the introducer 28. For example, the proximal end 53 of the inner surface 50 of the cap 46a may abut the section of the proximal insertion tip 40 that defines the opening 42, thereby preventing or reducing the risk of leakage from the opening. In one embodiment, the inner surface 50 of the cap 46a may abut the insertion tip 40 to form a liquid tight seal. The distal compartment 56 of cap 46a is sized to receive the flange 44 of the introducer 28 wherein the flange 44 engages and forms a snap or friction fit with the inner surface 50 of the cap 46a to removable secure the cap to the introducer. In the illustrated embodiment, optionally, the flange 44 of the introducer 28 abuts the shoulder 58 to form a seal that assists in reducing leakage from the catheter assembly. It will be understood that the cap 46*a* may be used with any of the introducers disclosed herein, including but not limited to the introducers disclosed in FIGS. 5, 15 and 16A.

Figure 6:
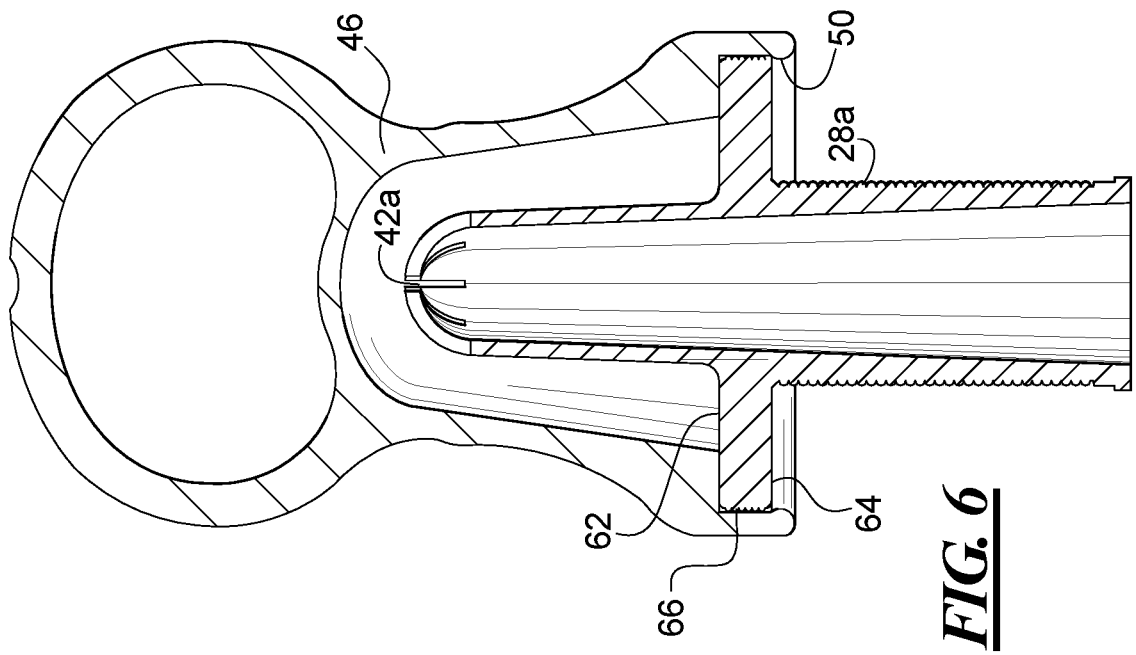
FIG. 6 is a cross-sectional view of the introducer of FIG. 5 shown engaged with a cap of the catheter assembly.
Figure 5:
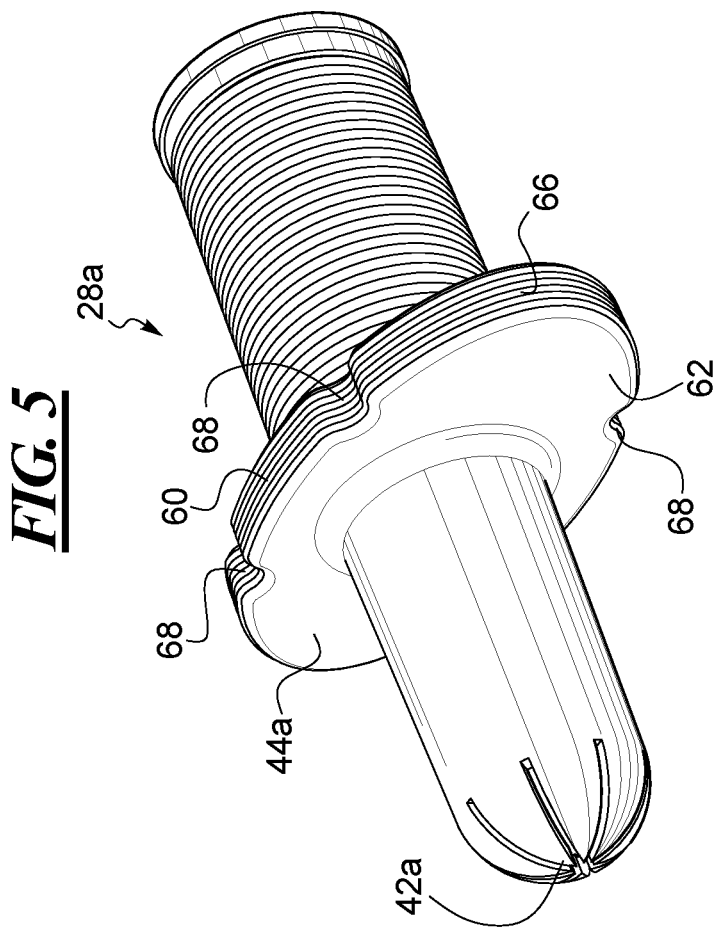
FIG. 5 is a perspective view of one embodiment of an introducer in accordance with the present disclosure.

FIGS. 5 and 6 illustrate an introducer 28*a* wherein the flange 44*a* includes a side surface 60 between the front and back surfaces 62 and 64 of the flange 44*a*. The side surface 60 includes surface textures, such as the illustrated plurality of grooves and ridges 66, that are configured to capture loose liquid which may leak from the opening 42*a* of the introducer 28*a* while the cap 46 is attached to the introducer 28*a* during storage and distribution. In another embodiment, the cap may be any of the caps disclosed here, such as those shown in FIG. 3, 7, 9, 17 or 18 and/or the introducer 28*a* may include any of the internal features disclosed herein, such as those shown in FIGS. 16 and 16A.

Referring to FIG. 6, when the cap 46 is removably connected to the introducer 28*a*, a space (including the grooves) is defined between the inner surface 50 of the cap 46 and the ridges. When the loose liquid enters this space, the liquid follows along the grooves and ridges and becomes captured or trapped, thus reducing the risk of leakage from the cap. For instance, if liquid were to leak from the opening 42*a* of the introducer 28*a*, the liquid may enter the grooves and become trapped. Optionally, the side surface 60 may include one or more indents 68 which may allow the liquid to enter grooves when the cap 46 is attached to the introducer 28*a*.

Figure 7:
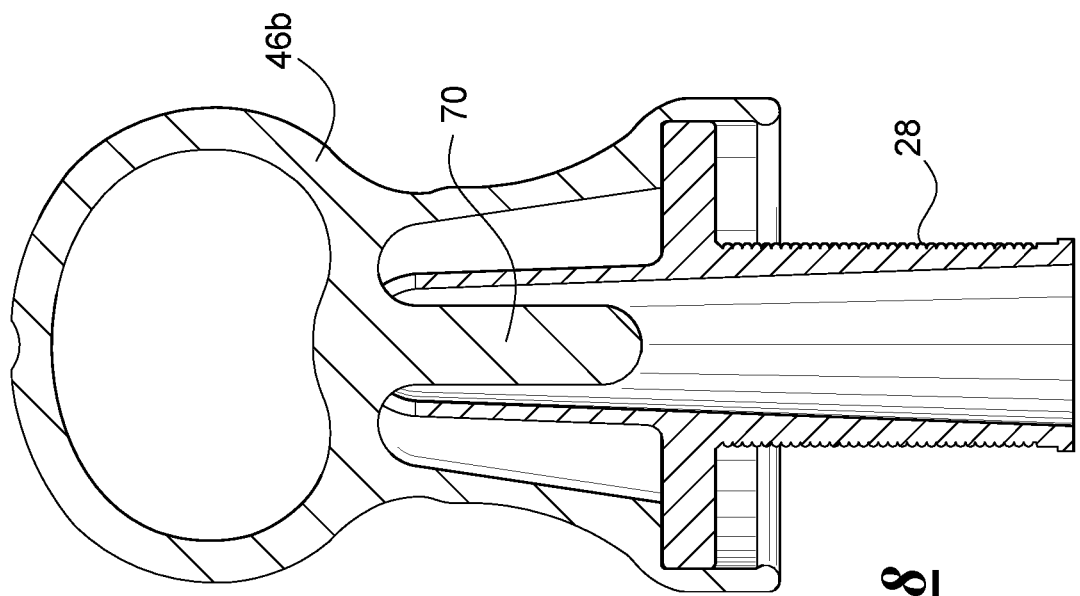
FIG. 7 is a cross-sectional view of one embodiment of a cap in accordance with the present disclosure.
Figure 8:
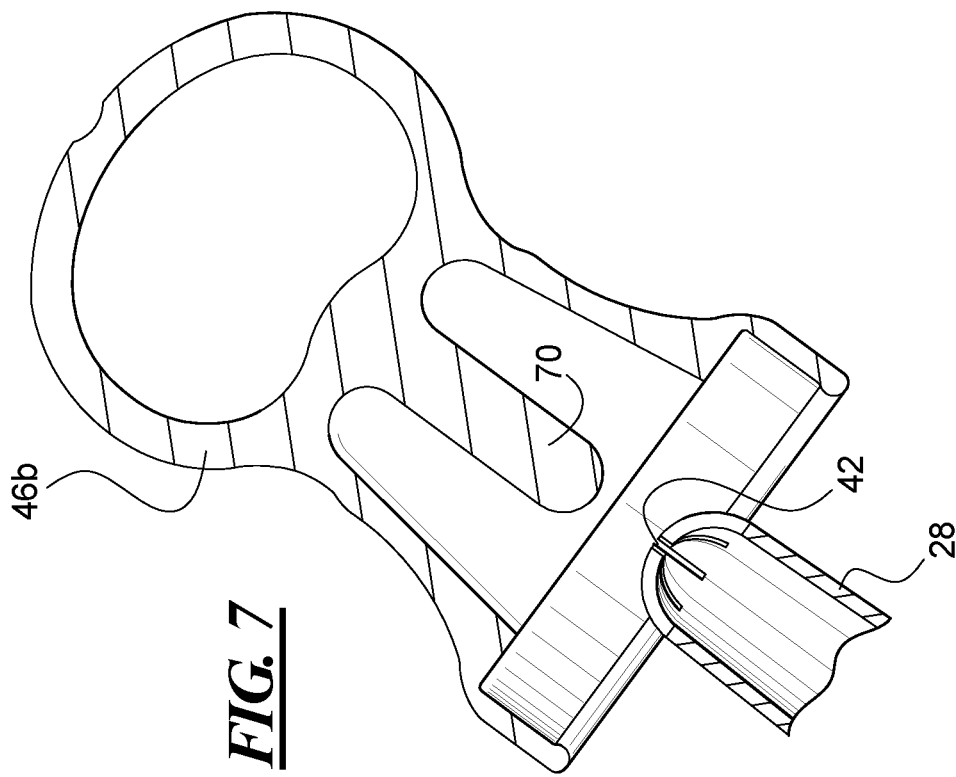
FIG. 8 is a cross-sectional view of the cap of FIG. 7 shown engaged with an introducer of the catheter assembly.

FIGS. 7 and 8 illustrate a cap 46*b* that includes a projection or extension or plug 70, which is shown as being elongated along a central axis of the cap 46*b*. While the projection 70 is illustrated as having a solid, substantially cylindrical configuration with a substantially uniform outer diameter, it is also within the scope of the present disclosure for the projection 70 to be differently configured (e.g., non-cylindrical).

When the cap 46*b* has been mounted onto the introducer 28, the projection 70 is at least partially positioned within the introducer 28, as shown in FIG. 8. The projection 70 extends through the proximal opening 42 of the introducer 28 (with the projection holding the opening 42 in an at least partially open configuration) to sealingly cooperate with the introducer 28 (or a component thereof) to provide a proximal seal. The projection 70 sealingly engages the introducer 28, thereby defining a liquid- or water-tight seal at the seal that prevents or reduces the risk of liquid leaking from the opening 42. It should be understood that the introducer could be any of those disclosed herein, such as those disclosed in FIGS. 5, 15, 16A, and 29, and the cap could include features disclosed in FIGS. 3, 17 and 19.

Figure 11:
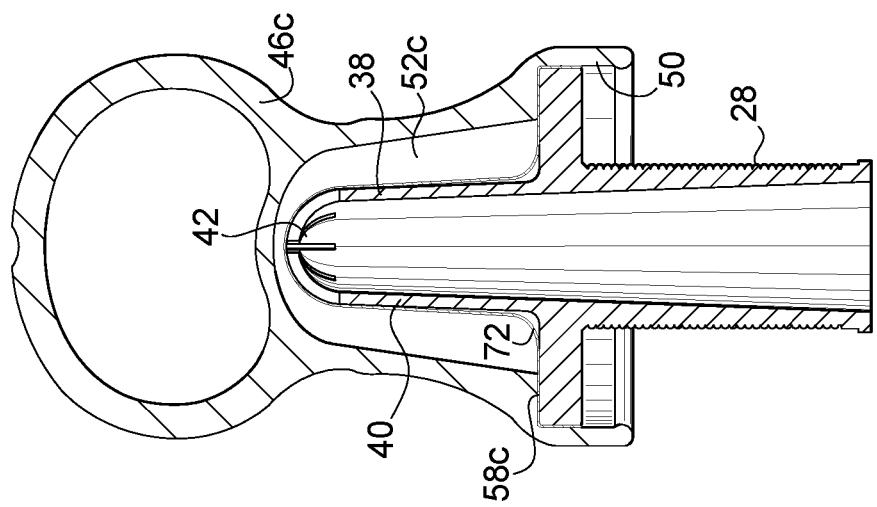
FIGS. 9-11 are cross-sectional views of a cap in accordance with the present disclosure wherein the cap is being placed over an introducer of the catheter assembly.
Figure 10:
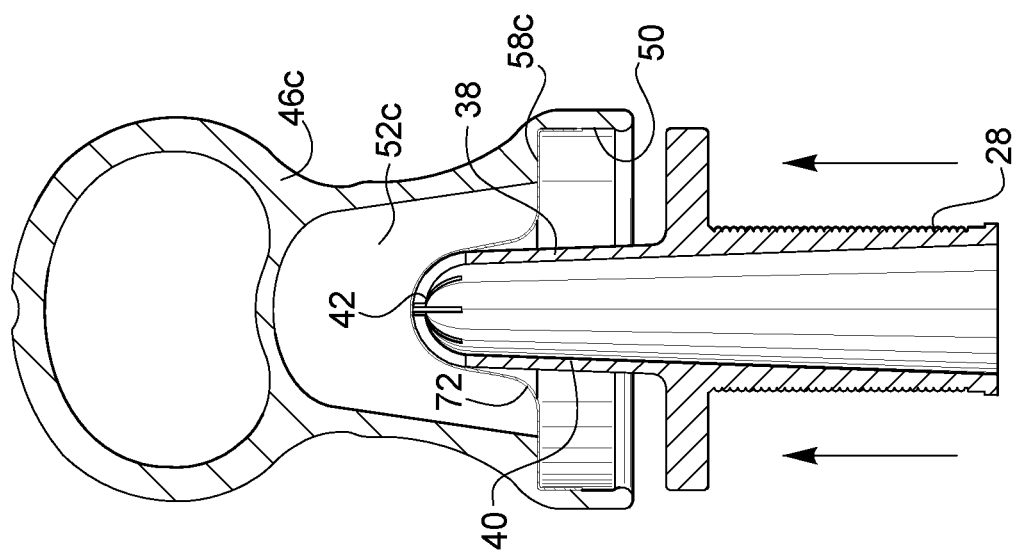
Figure 9:
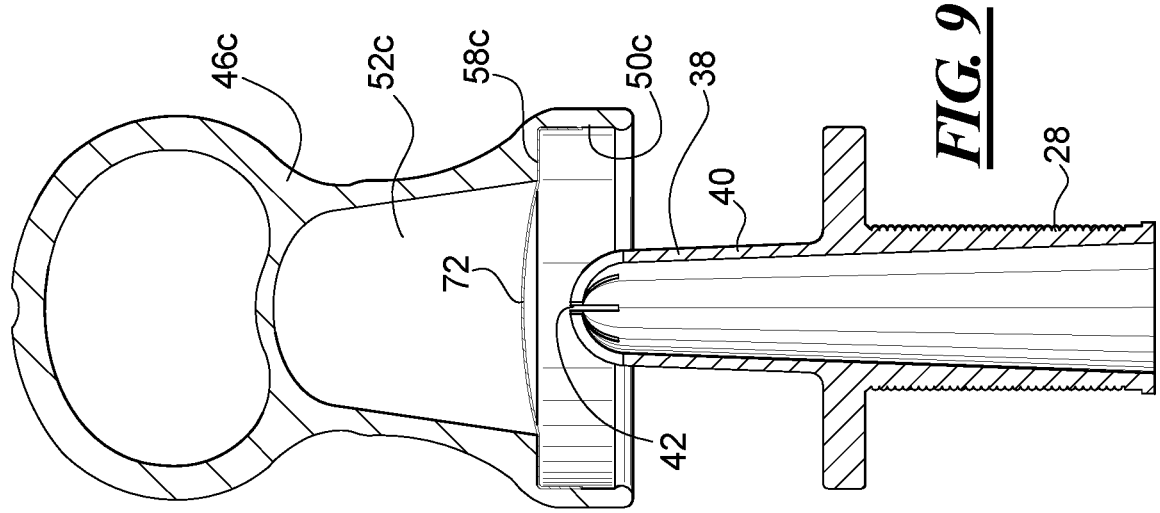

In FIGS. 9-10, the cap 46*c* includes an internal membrane 72 that is attached to the inner surface 50*c* of the cap 46*c*. The internal membrane 72 is stretchable and deformable such that when the proximal insertion tip 40 of the introducer 28 is inserted into the cavity 52*c* of the cap 46*c*, the internal membrane 72 stretches or deforms to cover at least the opening 42 of at the proximal end 38 of the introducer 28 and may cover substantially the entire insertion tip 40. In one embodiment, the internal membrane 72 conforms to and covers the entire insertion tip 42. The membrane 72 may be attached to the shoulder 58*c*. The membrane may be made from SEBS and/or SBS based thermoplastic elastomers, polyurethanes, polyethylenes, PVC, plasticized polyvinyl alcohol, and/or EVA. The membrane 72 may be elastic or partially elastic or permanently deformable. As shown in FIGS. 10 and 11, as the proximal insertion tip 40 of the introducer 28 is inserted into the cavity 52*c* of the cap 46*c*, the membrane 72 stretches and covers at least the opening 42 in the proximal insertion tip 40 of the introducer 28. The internal membrane 72 contacts the insertion tip 40 and forms a seal over the opening 42 to prevent liquid from leaking from the opening. It should be understood that the introducer could be any of those disclosed herein, such as those disclosed in FIGS. 5, 15, 16A, and 29.

FIGS. 12 and 13 illustrate another embodiment of a cap 74 which closely fits to the proximal end 38 of the introducer 28 and has a low profile. The cap 74 may be made from a polymer and/or an absorbent material. The cap 74 at least covers the opening 42 (FIG. 14) of the introducer 28 and contacts the portion of the insertion tip 40 defining the opening 42. The cap 74 forms a seal with the proximal end 38 of the introducer 28 to prevent or reduce the risk of liquid leaking from the opening 42. In one embodiment, the cap 74 extends distally to cover at least a portion of the insertion tip 40 of the introducer 28. In another embodiment, the cap 74 only covers a portion of the insertion tip 40. The cap 74 may be low-profile in that the wall 78 of the cap 74 may have a thickness of between about 0.1 mm and about 1 mm. As shown in FIG. 13, the cap 74 may, optionally, include a pull tab 76 that the user may pull to remove the cap 74 from the introducer 28. The pull tab 76 may be folded over the proximal end 80 of the cap 74 and releasably secured in place. The user may unfold the pull tab 76 to the position shown in FIG. 13 during removal of the cap 74. As shown in FIG. 14, the assembly may include two caps wherein cap 74 is an inner cap and cap 46 is an outer cap. When a pull tab 76 is utilized, the pull tab 76 may be connected to both the inner and outer caps 74 and 46 so that when the outer cap 46 is removed, the inner cap 74 is also removed. In other embodiments, the pull tab 76 may not be connected to the outer cap 46 and the user may be required to remove each cap individually. It should be understood that the introducer could be any of those disclosed herein, such as those disclosed in FIGS. 5, 15, 16A and 29.

Turning to FIGS. 15 and 16, the introducer 28*b* may include an absorbent material 82, such as but not limited to a sponge, located within the passageway 84 of the introducer 28*b*. The absorbent material 82 may absorb liquid and prevent or reduce the leakage of liquid from the opening 42*b* of the introducer 28*b*. The absorbent material 82 may service as or also be an applicator which may comprise a therapeutic agent, drug, lubricant, osmolality increasing agent, surfactant, salt, anti-bacterial agent and/or other substance with relevant clinical benefit to the user. The absorbent material 82 may be the same shape as the passageway 84. For example, in one embodiment, the absorbent material may be generally cylindrical. The absorbent material 82 also may be placed at any location within the passageway 84. In the illustrated embodiment, the absorbent material 82 is located in the midsection of the introducer 28*b*. The absorbent material 82 may define a passageway 86 configured to allow passage of the catheter shaft 16 therethrough, as shown in FIG. 16. The absorbent material 82 may also be configured to contact the catheter shaft 16 and remove excess liquid from the catheter shaft 16 as the catheter shaft passes through the passageway 86. FIG. 16A illustrates an embodiment wherein the introducer 28*b* has a cone shaped distal end portion 36*b* and the absorbent material 82*a* substantially occupies the cone shaped portion. It will be understood that the cap covering these introducers could be any of the caps disclosed herein, such as the caps illustrated in FIGS. 3, 17 and 19.

Figure 18:
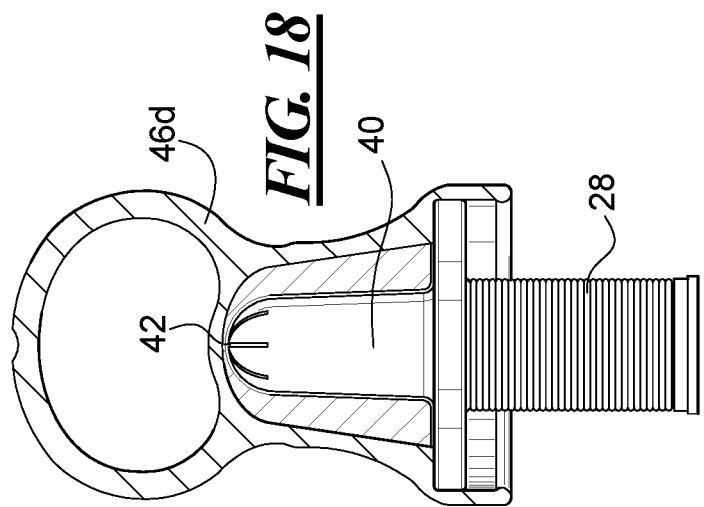
FIG. 18 is a cross-sectional view of the cap of FIG. 17 shown engaged with an introducer.
Figure 17:
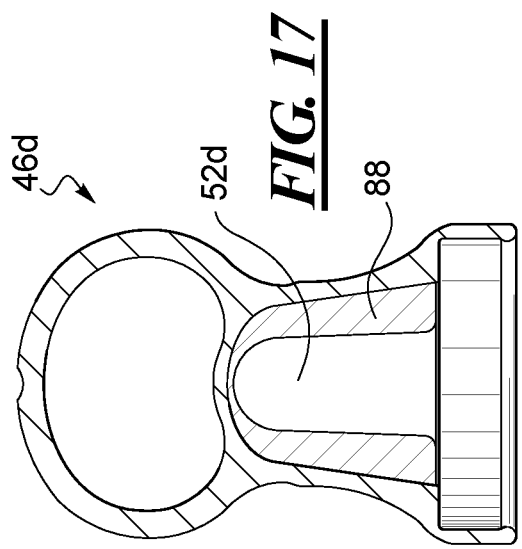
FIG. 17 is a cross-sectional view of another embodiment of a cap in accordance with the present disclosure.

Referring to FIGS. 17-20, the cap may include an absorbent material that is configured to absorb any liquid that may leak from opening 42 of the introducer 28. The absorbent material occupies at least a portion of the cavity of the cap. In FIGS. 17 and 18, cap 46d includes an absorbent material 88, such as a sponge, that is located in a portion of cavity 52d of the cap. In the illustrated embodiment, the absorbent material 88 is configured to surround at least a portion of the insertion tip 40 of the introducer 28 when the cap 46d covers the introducer (FIG. 18). In one embodiment, the absorbent material 88 includes an inner surface that is commensurate to the size and shape of the insertion tip 40. In another embodiment, the absorbent material may abut the insertion tip 40 such that the absorbent material 88 deforms to conform to the insertion tip 40.

Figure 20:
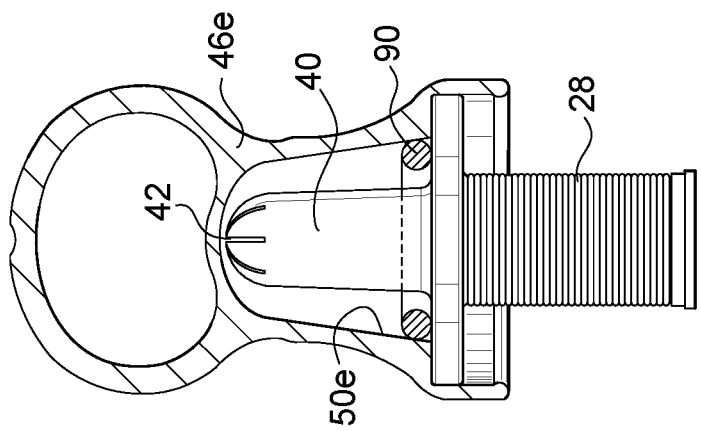
FIG. 20 is a cross-sectional view of another embodiment of a cap in accordance with the present disclosure shown engaged with an introducer.
Figure 19:
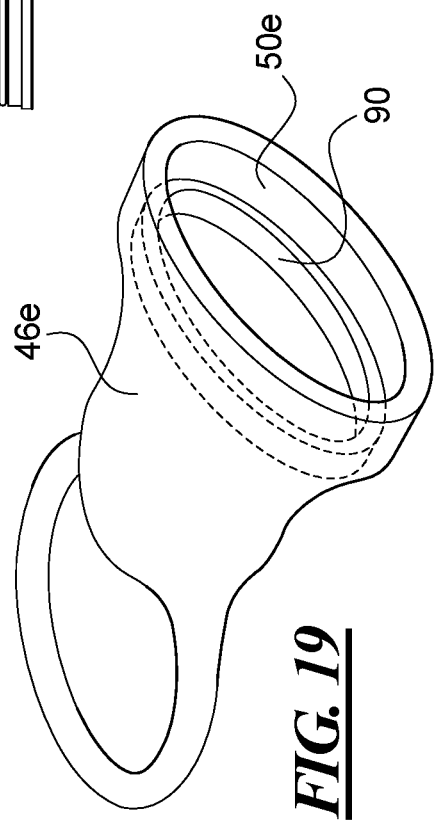
FIG. 19 is a perspective view of another embodiment of a cap in accordance with the present disclosure.

Turning to FIGS. 19 and 20, the cap 46e includes a ringed shaped absorbent member 90 that is attached to the inner surface 50e of the cap. In FIG. 19, the absorbent member 90 is shown as having a square cross-section and in FIG. 20, the absorbent member 90 is shown as having a circular cross-section. When the introducer 28 is inserted into the cap 46e, the absorbent material 90 may absorb any liquid that leaks from the opening 42 of the introducer 28.

FIG. 21 illustrates a catheter assembly 92 shown within an outer package 94. The catheter assembly 92 may be any of the catheter assemblies disclosed herein. The outer package 94 defines a cavity 96 containing the catheter assembly 92 and a first absorbent material 98 located at the proximal end 100 of the outer package 94 and a second absorbent material 102 located at the distal end 104 of the outer package 94. The absorbent material 98 and 102 may be, for example, sponge material, or superabsorbent fabric. Additionally, the absorbent material 98 and 102 may absorb any liquid that may leaks out of the catheter assembly so that there is no loose liquid in outer package 94, thereby reducing the risk of liquid spillage when the user opens the outer package 94. For example, the first absorbent material 98 may absorb any liquid that leaks from the introducer 28 and the second absorbent material 102 may absorb any liquid that may leak from drainage member 26. The absorbent materials may be placed at any location within the package. For example, the first absorbent material 98 may be located adjacent the introducer 28, and the second absorbent material 102 may be located adjacent the drainage member 26.

FIGS. 22-27 illustrate features and embodiments that prevent or reduce leakage of liquid from the distal opening of the drainage member 26. These features and embodiments may be used in a catheter assembly in combination with any of the cap, packaging, and/or tip features and embodiments disclosed herein. During storage and distribution, liquid within the sleeve may enter the catheter shaft 16 through the eyelets, and could potentially leak out of opening 27 in the distal end 34 of the drainage member 26. The features shown in FIGS. 22-27, seal or occlude the distal opening 27 so as to prevent or reduce the risk of leakage therefrom.

Turning to FIGS. 22-24, the catheter assembly may include a plug 110 that is inserted into the distal drainage opening 27 of the drainage member 26. The plug 110 forms a liquid tight seal with the drainage member 26 that prevents or reduces the risk of liquid leakage from the opening 27 of the drainage member 26. The plug 110 may have any shape that creates a seal with the drainage member 26. In the illustrated embodiment, the plug 110 has a substantially conical or tapered shape that is commensurate with that of the passage of the drainage member 26. Additionally, the plug may be solid or hollow.

Prior to use, the user removes the plug 110 and may drain any liquid that may be located in catheter shaft 16. With the plug removed, the opening 27 is unobstructed for urine drainage. As shown in FIGS. 23 and 24, the plug 110 may include a looped distal end 112 that can be used for grasping and pulling the plug 110 during removal from the drainage member 26.

FIGS. 25-27 illustrate covers that are attached to the distal end 34 of the drainage member 26 and cover the drainage opening to seal or occlude the opening. In the illustrated embodiment, the cover is attached to the rim 29 of the drainage member 26 that defines the opening of the drainage member. The cover may be attached to drainage member 26 by welding, heat sealing, adhesive, etc. Referring to FIG. 26, the cover 114 may be made from a material that does not dissolve or substantially dissolve when in contact with the liquid contained within the sleeve but dissolves when contacted with urine stream 113. In one embodiment, the cover 114 may be made from cellulose, poly vinyl alcohol, polyacrylic acid. As illustrated in FIG. 26, during use the cover 114 is dissolved by urine 116 such that the urine may drain from drainage opening 27.

Referring to FIG. 27, the cover 114a may be made from a material that does not dissolve but is required to be removed prior to use. The cover 114a includes a pull tab 116 that a user may pull to remove or peel the cover 114a from the drainage member 26 to open the drainage opening for urine drainage.

It will be understood that any the anti-leak features and embodiments shown in FIGS. 22-27 may be used in combination with any of cap, introducer and packaging features disclosed herein.

FIGS. 28-31 illustrate venting features/members of the catheter assembly which allow air (gases) to be vented from the compartment of the sleeve while the sleeve is being collapsed during insertion of the catheter into the user. Because the sleeve is sealed or otherwise configured to retain liquid therein, if gases within the sleeve are not vented or allowed to escape during collapsing of the sleeve, the pressure within the sleeve may increase. Increased pressure within the collapsing sleeve may cause some resistance to collapsing of the sleeve as the catheter is inserted into the patient. Allowing gases to vent from the sleeve reduces pressure within the collapsing sleeve, thereby allowing the sleeve to easily collapse during use. The venting features disclosed herein may be used in combination with any of the other features disclosed herein.

Referring to FIG. 28, the catheter assembly 120 may include several features similar to that of catheter assembly 10 of FIG. 1. Catheter assembly 120 may including a sleeve 122 wherein a portion of the sleeve includes a membrane or membrane portion 124 that is gas permeable but liquid impermeable. The membrane 124 may be the same material as the sleeve 122 wherein the membrane 124 is a portion of the sleeve that has been conditioned to allow gas permeability. For example, the membrane portion of the sleeve 112 may have been stretched or impregnated with a composition that results in gas permeability of the membrane portion. In one embodiment, the sleeve 122 may be made from polyethylene and/or polyurethane material. The material may be conditioned by enabling micropores through which gas can flow but liquid cannot flow through due to the high viscosity and surface tension of the liquid. This makes a portion of the sleeve gas permeable and liquid impermeable. In other embodiments, the membrane 124 may be a separate component that is attached to the remaining portion of the sleeve 122.

Turning to FIG. 29, the introducer 126 may include vents 128, such as passageways therethrough, that are in communication with the compartment defined by the sleeve. The vents 128 may be gas permeable, liquid impermeable vents. For example, a gas permeable, liquid impermeable membrane (not shown) may be associated with the vent 128 so as to allow the passage of gases but prevent the passage of liquid. In one embodiment, the membrane may cover the vent 128 and in another embodiment, the membrane may be located within the vent.

Turing to FIGS. 30 and 31, the drainage member 130 may include gas permeable, liquid impermeable vents 132 that are in communication with the compartment defined by the sleeve. For example, a gas permeable, liquid impermeable membrane (not shown) may be associated with the vent 132 so as to allow the passage of gases but prevent the passage of liquid. In one embodiment, the membrane may cover the vent 132 and in another embodiment, the membrane may be located within the vent.

Figure 32:
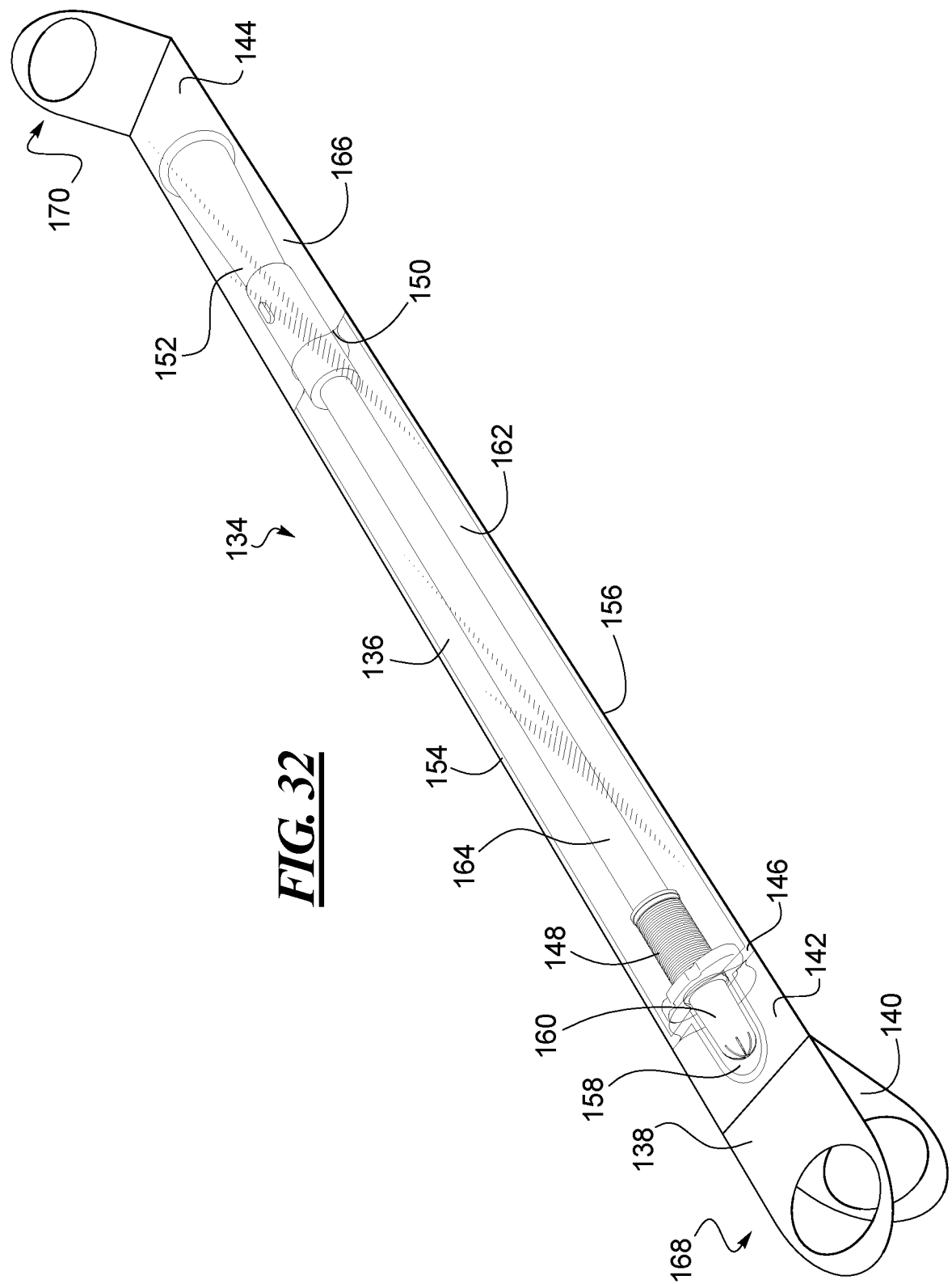
FIG. 32 is another embodiment of a catheter assembly in accordance with the present disclosure.

FIG. 32 illustrates a catheter assembly 134 that includes a sleeve 136 formed from a front sheet 138 and back sheet 140 that are sealed to each other. The sleeve 136 includes a proximal seal 142 and a distal seal 144. The sleeve 136 also includes intermediate seals wherein the first or proximal intermediate seal 146 is sealed to an introducer 148 and a second or distal intermediate seal 150 is sealed to the drainage member 152. The sleeve 136 also includes opposed side seals 154, 156. A proximal compartment 158 is defined between the proximal seal 142 and the first intermediate seal 146 wherein the proximal compartment 158 contains the insertion tip 160 of the introducer 148. In the illustrated embodiment, the proximal compartment 158 is commensurate or closely follows the size and shape of the insertion tip 160 of the introducer 148. An intermediate compartment 162 is defined between the first and second intermediate seals 146 and 150. The intermediate compartment 162 contains at least the catheter shaft 164 and a liquid (not shown) that enhances the lubricity of the catheter. A distal compartment 166 is defined between the second intermediate seal 150 and the distal end seal 144 wherein the distal compartment 166 contains at least a portion of the drainage member 152.

The sheets include unsealed proximal end portions 168 proximal of the proximal seal 142 and unsealed distal end portions 170 distal of the distal seal 144. During use, the user grasps the unsealed proximal end portions 168 of the sheets and pulls them apart to open the proximal compartment 158, thereby exposing the introducer 148. The user also grasps the unsealed distal end portions 170 of the sheets and pulls them apart to open the distal compartment 166 thereby exposing the drainage member 152. The user may then insert the introducer 148 into the urethra and utilize the sleeve 136 to insert the catheter shaft.

It should be understood that various changes and modifications to the presently preferred embodiments described herein will be apparent to those skilled in the art. Such changes and modification can be made without departing from the spirit and scope of the invention disclosed herein.

What is claimed is:

1. A catheter assembly comprising:
    a urinary catheter comprising a shaft with a proximal end portion and a distal end portion, the shaft having a hydrophilic surface;
    a collapsible sleeve defining a compartment that contains at least a portion of the catheter shaft, a distal end portion of the sleeve being attached to the distal portion of the urinary catheter;
    a wetting fluid located within the compartment of the sleeve;
    an introducer located at a proximal end of the sleeve, wherein the introducer includes a proximal introducer tip, an introducer distal portion, and a flange located between the proximal introducer tip and introducer distal portion, the collapsible sleeve being attached to the introducer distal portion;
    a removable cap covering the introducer, wherein the cap defines a cavity that receives the introducer tip;
    the cavity including a cavity proximal compartment and a cavity distal compartment that is wider than the cavity proximal compartment and is located adjacent to the cavity proximal compartment, wherein the cavity distal compartment is configured to receive a flange located at a distal end of the introducer tip; and
    an absorbent material located in the cavity that absorbs fluid leaking from the sleeve.

2. The catheter assembly of claim 1, wherein the absorbent material surrounds at least a portion of the introducer tip.

3. The catheter assembly of claim 2, wherein the cavity is defined by an internal surface of the cap and the absorbent material is located on the internal surface of the cap.

4. The catheter assembly of claim 3, wherein the absorbent material covers at least a portion of the internal surface defining the cavity proximal compartment.

5. The catheter assembly of claim 4, wherein the absorbent material covers the entire internal surface defining the cavity proximal compartment.

6. The catheter assembly of claim 5, wherein the absorbent material comprises an inner surface defining an inner cavity shaped to receive the introducer tip.

7. The catheter assembly of claim 6, wherein the inner surface is commensurate to the size and shape of the introducer tip.

8. The catheter assembly of claim 5, wherein the absorbent material comprises a deformable material configured to contact and conform to the shape of the introducer tip.

9. The catheter assembly of claim 2, wherein the absorbent material comprises a ring on an internal surface of the cavity.

10. The catheter assembly of claim 1, wherein the absorbent material is a sponge.

11. A leak resistant cap for a urinary catheter assembly comprising:
    a closed proximal end and an open distal end;
    an internal surface defining a cavity located at the open distal end, wherein the cavity is sized and configured to receive a proximal end of an introducer of the urinary catheter assembly and the urinary catheter assembly having a wetting liquid;
    the cavity including a cavity proximal compartment and a cavity distal compartment that is wider than the cavity proximal compartment and is located adjacent to the cavity proximal compartment, wherein the cavity distal compartment is configured to receive a flange of the urinary catheter assembly; and
    an absorbent material located in the cavity proximal compartment, wherein the absorbent material absorbs the wetting liquid leaking from the urinary catheter assembly, thereby preventing leakage from the urinary catheter assembly.

12. The cap of claim 11, wherein the absorbent material surrounds at least a portion of the proximal end of the urinary catheter assembly.

13. The cap of claim 12, wherein the absorbent material is located on the internal surface of the cap.

14. The cap of claim 13, wherein the absorbent material covers at least a portion of the internal surface defining the cavity proximal compartment.

15. The cap of claim 14, wherein the absorbent material covers the entire internal surface defining the cavity proximal compartment.

16. The cap of claim 15, wherein the absorbent material comprises an inner surface defining an inner cavity shaped to receive the proximal end of the catheter assembly.

17. The cap of claim 16, wherein the inner surface is commensurate to the size and shape of the proximal end of the catheter assembly.

18. The cap of claim 15, wherein the absorbent material comprises a deformable material configured to contact and conform to the shape of the proximal end of the catheter assembly.

19. A catheter assembly comprising:
   a urinary catheter comprising a shaft with a proximal end portion and a distal end portion, the shaft having a hydrophilic surface;
   a collapsible sleeve defining a compartment that contains at least a portion of the catheter shaft, a distal end portion of the sleeve being attached to the distal portion of the urinary catheter;
   a wetting fluid located within the compartment of the sleeve;
   an introducer comprising a tip and located at a proximal end of the sleeve;
   a removable cap covering the introducer, wherein the cap defines a cavity that receives the introducer tip; and
   a superabsorbent material located in the cavity configured to absorb fluid leaking from the sleeve.

20. A leak resistant cap for a urinary catheter assembly comprising:
   a closed proximal end and an open distal end;
   an internal surface defining a cavity located at the open distal end, wherein the cavity is sized and configured to receive a proximal end of an introducer of the urinary catheter assembly and the urinary catheter assembly having a wetting liquid; and
   a superabsorbent material located in the cavity, wherein the superabsorbent material absorbs the wetting liquid leaking from the urinary catheter assembly, thereby preventing leakage from the urinary catheter assembly.

* * * * *